(12) United States Patent
Wang

(10) Patent No.: US 10,307,277 B2
(45) Date of Patent: Jun. 4, 2019

(54) METHOD OF UNIFORM CRIMPING AND EXPANSION OF MEDICAL DEVICES

(71) Applicant: Abbott Cardiovascular Systems Inc., Santa Clara, CA (US)

(72) Inventor: Yunbing Wang, Sunnyvale, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 0 days.

(21) Appl. No.: 15/627,337

(22) Filed: Jun. 19, 2017

(65) Prior Publication Data
US 2017/0348124 A1    Dec. 7, 2017

Related U.S. Application Data

(63) Continuation of application No. 13/644,347, filed on Oct. 4, 2012, now Pat. No. 9,724,219.

(51) Int. Cl.
| | | |
|---|---|---|
| *A61F 2/95* | (2013.01) | |
| *A61M 25/10* | (2013.01) | |
| *B23P 11/00* | (2006.01) | |
| *A61F 2/958* | (2013.01) | |
| *A61F 2/91* | (2013.01) | |

(52) U.S. Cl.
CPC ............... *A61F 2/958* (2013.01); *A61F 2/91* (2013.01); *A61F 2002/9522* (2013.01); *A61F 2002/9583* (2013.01); *A61M 25/1025* (2013.01); *B23P 11/00* (2013.01); *Y10T 29/49863* (2015.01)

(58) Field of Classification Search
CPC .............................. B23P 11/00; B23P 11/005; A61M 25/1025; A61M 25/1034; A61M 2025/1027; A61F 2/95; A61F 2002/9583; Y10T 29/49826; Y10T 29/49908; Y10T 29/49913
See application file for complete search history.

(56) References Cited

U.S. PATENT DOCUMENTS

| | | |
|---|---|---|
| 5,261,263 A | 11/1993 | Whitesell |
| 5,556,383 A | 9/1996 | Wang et al. |
| 5,672,169 A | 9/1997 | Verbeek |
| 5,836,965 A | 11/1998 | Jendersee et al. |
| 5,913,871 A | 6/1999 | Werneth et al. |
| 5,976,181 A | 11/1999 | Whelan et al. |

(Continued)

FOREIGN PATENT DOCUMENTS

| | | |
|---|---|---|
| CN | 1260213 | 7/2000 |
| CN | 101015440 | 8/2007 |

(Continued)

OTHER PUBLICATIONS

U.S. Appl. No. 13/089,225, filed Apr. 18, 2011, Roberts et al.
(Continued)

*Primary Examiner* — Christopher J Besler
(74) *Attorney, Agent, or Firm* — Squire Patton Boggs (US) LLP

(57) ABSTRACT

A medical device-includes a scaffold crimped to a catheter having an expansion balloon. The scaffold is crimped to the balloon by a process that includes one or more balloon pressurization steps. The balloon pressurization steps are selected to enhance scaffold retention to the balloon, maintain a relatively uniform arrangement of balloon folds about the inner surface of the crimped scaffold so that the scaffold expands in a uniform manner when the balloon is inflated, and to avoid any possible over-stretching of balloon material.

19 Claims, 13 Drawing Sheets

(56) References Cited

U.S. PATENT DOCUMENTS

| | | | |
|---|---|---|---|
| 5,992,000 A | 11/1999 | Humphrey et al. |
| 6,018,857 A | 2/2000 | Duffy et al. |
| 6,063,092 A | 5/2000 | Shin |
| 6,092,526 A | 7/2000 | LaFontaine et al. |
| 6,179,867 B1 | 1/2001 | Cox |
| 6,305,436 B1 | 10/2001 | Andersen et al. |
| 6,312,459 B1 | 11/2001 | Huang et al. |
| 6,360,577 B2 | 3/2002 | Austin |
| 6,488,688 B2 | 12/2002 | Lim et al. |
| 6,629,350 B2 | 10/2003 | Motsenbocker |
| 6,666,880 B1 | 12/2003 | Chiu et al. |
| 6,745,445 B2 | 6/2004 | Spilka |
| 6,783,542 B2 | 8/2004 | Eidenschink |
| 6,805,703 B2 | 10/2004 | McMorrow |
| 6,863,683 B2 | 3/2005 | Schwager et al. |
| 6,931,899 B2 | 8/2005 | Goff et al. |
| 7,010,850 B2 | 3/2006 | Hijlkema et al. |
| 7,156,869 B1 | 1/2007 | Pacetti |
| 7,316,148 B2 | 1/2008 | Asmus et al. |
| 7,389,670 B1 | 6/2008 | Kokish et al. |
| 7,563,400 B2 | 7/2009 | Wilson et al. |
| 7,648,727 B2 | 1/2010 | Hossainy et al. |
| 7,761,968 B2 | 7/2010 | Huang et al. |
| 7,762,804 B1 | 7/2010 | Stupecky |
| 7,763,198 B2 | 7/2010 | Knott et al. |
| 7,886,419 B2 | 2/2011 | Huang et al. |
| 7,945,409 B2 | 5/2011 | Furst et al. |
| 7,947,207 B2 | 5/2011 | McNiven et al. |
| 7,951,185 B1 | 5/2011 | Abbate et al. |
| 7,971,333 B2 | 7/2011 | Gale et al. |
| 8,002,817 B2 | 8/2011 | Limon |
| 8,046,897 B2 | 11/2011 | Wang et al. |
| 8,123,793 B2 | 2/2012 | Roach et al. |
| 8,225,474 B2 | 7/2012 | Arcand et al. |
| 8,261,423 B2 | 9/2012 | Jow et al. |
| 8,323,760 B2 | 12/2012 | Zheng et al. |
| 8,425,587 B2 | 4/2013 | Trollsas et al. |
| 8,539,663 B2 | 9/2013 | Wang |
| 8,595,913 B2 | 12/2013 | Knott et al. |
| 8,726,483 B2 | 5/2014 | Stankus et al. |
| 8,752,261 B2 | 6/2014 | Van Sciver |
| 8,752,265 B2 | 6/2014 | Wang |
| 8,844,113 B2 | 9/2014 | Wang |
| 8,961,848 B2 | 2/2015 | Roberts et al. |
| 9,155,870 B2 | 10/2015 | Wang |
| 9,199,408 B2 | 12/2015 | Wang et al. |
| 9,283,100 B2 | 3/2016 | Wang et al. |
| 9,308,106 B2 | 4/2016 | Knott et al. |
| 9,642,729 B2 | 5/2017 | Wang et al. |
| 9,681,971 B2 | 6/2017 | Wang |
| 9,724,219 B2 | 8/2017 | Wang |
| 9,895,241 B2 | 2/2018 | Wang |
| 9,931,787 B2 | 4/2018 | Harrington et al. |
| 9,999,527 B2 | 6/2018 | Pacetti et al. |
| 2002/0035774 A1 | 3/2002 | Austin |
| 2002/0143382 A1 | 10/2002 | Hijlkema et al. |
| 2003/0070469 A1 | 4/2003 | Kokish |
| 2004/0078953 A1 | 4/2004 | Spilka |
| 2004/0096538 A1 | 5/2004 | Goff et al. |
| 2004/0106973 A1 | 6/2004 | Johnson |
| 2004/0138731 A1 | 7/2004 | Johnson |
| 2004/0181236 A1 | 9/2004 | Eidenschink et al. |
| 2004/0260379 A1 | 12/2004 | Jagger et al. |
| 2005/0119720 A1 | 6/2005 | Gale et al. |
| 2005/0143752 A1 | 6/2005 | Schwager et al. |
| 2005/0159802 A1 | 7/2005 | Furst et al. |
| 2005/0183259 A1 | 8/2005 | Eidenschink et al. |
| 2005/0188525 A1 | 9/2005 | Weber et al. |
| 2005/0229670 A1 | 10/2005 | Perreault |
| 2005/0244533 A1 | 11/2005 | Motsenbocker et al. |
| 2005/0283225 A1 | 12/2005 | Klisch |
| 2006/0004469 A1 | 1/2006 | Sokel |
| 2006/0047336 A1 | 3/2006 | Gale et al. |
| 2006/0100694 A1 | 5/2006 | Globerman |
| 2006/0116748 A1 | 6/2006 | Kaplan et al. |
| 2006/0123874 A1 | 6/2006 | Motsenbocker |
| 2006/0196073 A1 | 9/2006 | Parker |
| 2007/0006441 A1 | 1/2007 | McNiven et al. |
| 2007/0023974 A1 | 2/2007 | Wu |
| 2007/0204455 A1 | 9/2007 | Knott et al. |
| 2007/0259099 A1 | 11/2007 | Van Sciver |
| 2007/0271763 A1 | 11/2007 | Huang et al. |
| 2007/0282433 A1 | 12/2007 | Limon et al. |
| 2007/0289117 A1 | 12/2007 | Huang et al. |
| 2007/0293938 A1 | 12/2007 | Gale et al. |
| 2008/0016668 A1 | 1/2008 | Huang et al. |
| 2008/0033523 A1 | 2/2008 | Gale et al. |
| 2008/0033524 A1 | 2/2008 | Gale |
| 2008/0033526 A1 | 2/2008 | Atladottir et al. |
| 2008/0072653 A1 | 3/2008 | Gillick et al. |
| 2008/0127707 A1 | 6/2008 | Kokish et al. |
| 2008/0147164 A1 | 6/2008 | Gale et al. |
| 2008/0208327 A1 | 8/2008 | Rowe |
| 2008/0275537 A1 | 11/2008 | Limon |
| 2009/0001633 A1 | 1/2009 | Limon et al. |
| 2009/0088829 A1 | 4/2009 | Wang et al. |
| 2009/0105800 A1 | 4/2009 | Sabaria |
| 2009/0133817 A1 | 5/2009 | Sabaria |
| 2009/0228094 A1 | 9/2009 | Yan et al. |
| 2009/0282669 A1 | 11/2009 | von Oepen et al. |
| 2009/0287289 A1 | 11/2009 | Sagedahl et al. |
| 2009/0299452 A1 | 12/2009 | Eidenschink et al. |
| 2010/0004735 A1 | 1/2010 | Yang et al. |
| 2010/0025894 A1 | 2/2010 | Kleiner et al. |
| 2010/0063571 A1 | 3/2010 | Roch et al. |
| 2010/0115755 A1 | 5/2010 | Pacetti |
| 2010/0286758 A1 | 11/2010 | Berglund |
| 2010/0323091 A1 | 12/2010 | Castro et al. |
| 2011/0152905 A1 | 6/2011 | Eaton |
| 2011/0190872 A1 | 8/2011 | Anukhin et al. |
| 2011/0270383 A1 | 11/2011 | Jow et al. |
| 2011/0271513 A1 | 11/2011 | Wang |
| 2011/0307046 A1 | 12/2011 | Bourang et al. |
| 2012/0010693 A1 | 1/2012 | Van Sciver |
| 2012/0017416 A1 | 1/2012 | Wang et al. |
| 2012/0042501 A1 | 2/2012 | Wang et al. |
| 2012/0079706 A1 | 4/2012 | Knott et al. |
| 2012/0285609 A1 | 11/2012 | Wang |
| 2012/0316635 A1 | 12/2012 | Jow et al. |
| 2013/0255853 A1 | 10/2013 | Wang et al. |
| 2014/0033506 A1 | 2/2014 | Jow et al. |
| 2014/0096357 A1 | 4/2014 | Wang |
| 2014/0189994 A1 | 7/2014 | Van Sciver |
| 2014/0230225 A1 | 8/2014 | Van Sciver |
| 2014/0336747 A1 | 11/2014 | Rapoza et al. |
| 2015/0059960 A1 | 3/2015 | Roberts et al. |
| 2015/0257907 A1 | 9/2015 | Vial et al. |
| 2016/0081824 A1 | 3/2016 | Harrington et al. |
| 2018/0116830 A1 | 5/2018 | Wang |
| 2018/0228630 A1 | 8/2018 | Wang et al. |

FOREIGN PATENT DOCUMENTS

| | | |
|---|---|---|
| EP | 0 787 020 | 8/1997 |
| EP | 1 000 591 | 5/2000 |
| EP | 1 226 798 | 7/2002 |
| EP | 1 295 570 | 3/2003 |
| EP | 1 818 073 | 8/2007 |
| EP | 2 029 052 | 3/2009 |
| JP | 2005-535459 | 11/2005 |
| JP | 2008-538940 | 11/2008 |
| JP | 2009-540928 | 11/2009 |
| JP | 2009-542263 | 12/2009 |
| JP | 2010-525903 | 7/2010 |
| JP | 2010-540091 | 12/2010 |
| WO | WO 99/55406 | 11/1999 |
| WO | WO 00/36994 | 6/2000 |
| WO | WO 01/35861 | 5/2001 |
| WO | WO 02/074192 | 9/2002 |
| WO | WO 02/102283 | 12/2002 |
| WO | WO 2004/016369 | 2/2004 |
| WO | WO 2005/053937 | 6/2005 |
| WO | WO 2006/110861 | 10/2006 |
| WO | WO 2006/117016 | 11/2006 |

(56) References Cited

FOREIGN PATENT DOCUMENTS

| WO | WO 2007/116305 | 10/2007 |
| WO | WO 2007/146354 | 12/2007 |
| WO | WO 2007/146543 | 12/2007 |
| WO | WO 2007/149464 | 12/2007 |
| WO | WO2008/011028 | 1/2008 |
| WO | WO 2008/033621 | 3/2008 |
| WO | WO 2008/137821 | 11/2008 |
| WO | WO 2009/045764 | 4/2009 |
| WO | WO 2010/036982 | 4/2010 |
| WO | WO 2010/151497 | 12/2010 |
| WO | WO2011/136929 | 11/2011 |
| WO | WO 2012/006451 | 1/2012 |
| WO | WO2012/027172 | 1/2012 |
| WO | WO 2012/044454 | 4/2012 |
| WO | WO 2013/039637 | 3/2013 |

OTHER PUBLICATIONS

U.S. Appl. No. 13/194,162, filed Apr. 29, 2011, Stankus et al.
U.S. Appl. No. 13/438,211, filed Apr. 3, 2012, Yunbing et al.
U.S. Appl. No. 13/473,031, filed May 16, 2012, Wang et al.
Bosiers et al., "Coronary and endovascular applications of the Absorb™ bioresorbable vascular scaffold", Interv. Cardiol. 4(6), pp. 621-631 (2012).
Japanese Office Action dated Jul. 25, 2017, Japanese Patent Application No. 2015-535672, machine translation of Japanese Office Action to English, 4 pages (2017).
Miller "Abbott's Bioresorbable Stent Shows Durable Results in Absorb Trial", The Gray Sheet, pp. 17-18, Mar. 2003.
U.S. Appl. No. 11/330,927, filed Jan. 11, 2006, Wu et al.
U.S. Appl. No. 11/938,127, filed Nov. 9, 2007, Wang.
Angioplasty Summit Abstracts/Oral, Am J Cardiol. Apr. 23-26, 2013, p. 23B.
Zhang et al., "Heparin-and basic fibroblast growth factor-incorporated degradable stent: comparison with traditional transmyocardial revascularization", J Cardiovasc Surg. 2011; 52: 261-270.

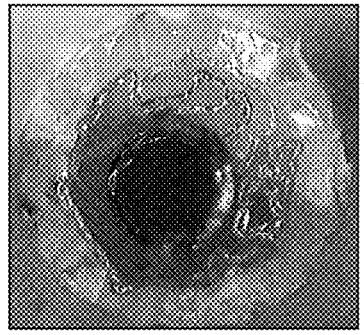 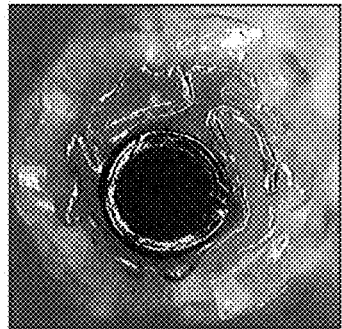 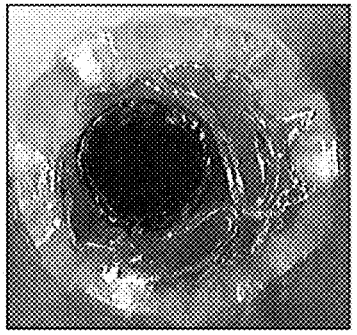
FIG. 8A          FIG. 8B          FIG. 8C
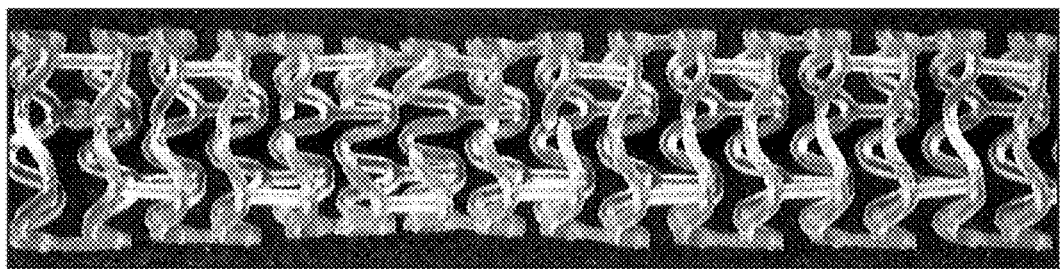
FIG. 9

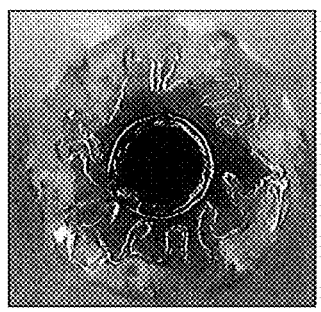 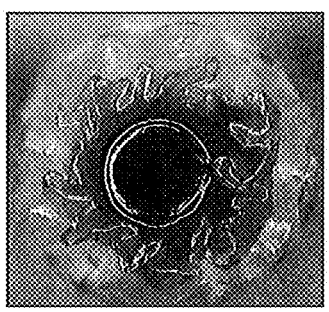 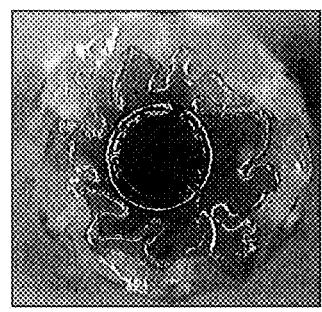
FIG. 10A  FIG. 10B  FIG. 10C
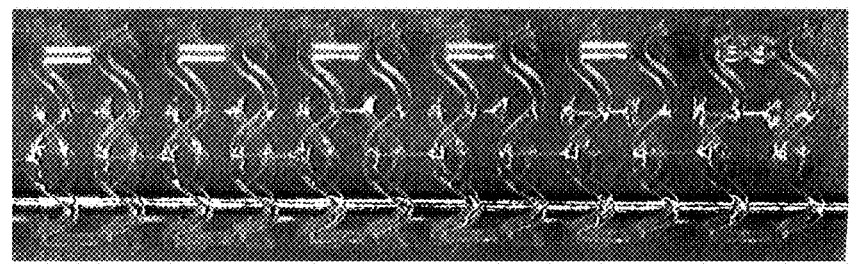
FIG. 11

METHOD OF UNIFORM CRIMPING AND EXPANSION OF MEDICAL DEVICES

BACKGROUND OF THE INVENTION

Field of the Invention

The present invention relates to medical devices; more particularly, this invention relates to processes for uniformly crimping and deploying a medical device, such as a polymeric scaffold, to and from, respectively, a delivery balloon.

BACKGROUND OF THE INVENTION

The art recognizes a variety of factors that affect a polymeric scaffold's/stent's ability to retain its structural integrity when subjected to external loadings, such as crimping and balloon expansion forces. According to the art, characteristics differentiating a polymeric, bio-absorbable scaffolding of the type expanded to a deployed state by plastic deformation from a similarly functioning metal stent are many and significant. Indeed, several of the accepted analytic or empirical methods/models used to predict the behavior of metallic stents tend to be unreliable, if not inappropriate, as methods/models for reliably and consistently predicting the highly non-linear behavior of a polymeric load-bearing portion of a balloon-expandable scaffold (hereinafter "scaffold"). The models are not generally capable of providing an acceptable degree of certainty required for purposes of implanting the scaffold within a body, or predicting/anticipating the empirical data.

Polymer material considered for use as a polymeric scaffold, e.g. poly(L-lactide) ("PLLA"), poly(L-lactide-co-glycolide) ("PLGA"), poly(D-lactide-co-glycolide) or poly (L-lactide-co-D-lactide) ("PLLA-co-PDLA") with less than 10% D-lactide, and PLLD/PDLA stereo complex, may be described, through comparison with a metallic material used to form a stent, in some of the following ways. A suitable polymer has a low strength to weight ratio, which means more material is needed to provide an equivalent mechanical property to that of a metal. Therefore, struts must be made thicker and wider to have the required strength for a stent to support lumen walls at a desired radius. The scaffold made from such polymers also tends to be brittle or have limited fracture toughness. The anisotropic and rate-dependant inelastic properties (i.e., strength/stiffness of the material varies depending upon the rate at which the material is deformed) inherent in the material, only compound this complexity in working with a polymer, particularly, bio-absorbable polymer such as PLLA or PLGA.

One challenge to a scaffold/stent is uniformly crimping to a balloon and uniform expansion of the scaffold when the balloon is inflated. In the case of a polymeric scaffold, problems arise where, on the one hand, the scaffold cannot be crimped to the desired size without introducing structural failure, i.e., fracture, or excessive cracking, either in the crimped state or when expanded from the crimped state by a balloon. On the other hand, a scaffold can be crimped and deployed, yet deploys with non-uniformity in its deployed state. In these cases the scaffold is susceptible to acute or fatigue failure as the irregularly-deployed rings and/or cells, loaded beyond their design limits as a consequence of the non-uniform deployment, have a reduced acute or fatigue life within the vessel.

Additionally, the retention force keeping a crimped scaffold on a delivery balloon during transit through tortuous anatomy is sometimes not sufficiently high to preclude pre-mature dislodgment of the scaffold from the balloon. If the scaffold is not held on the balloon with sufficient force, e.g., as where there is recoil in the scaffold following crimping or the coefficient of friction between balloon and scaffold is too low, the scaffold can become separated from the balloon as the catheter distal end flexes and/or impinges on walls of the delivery sheath. For a metallic stent, there are several well-known approaches for increasing the retention of the stent to a balloon during transit to the target site. However, methods proposed thus far for retaining the scaffold on a balloon are in need of improvement, or inappropriate for a polymer scaffold.

In one example of a method for crimping a metallic stent to a delivery balloon, the stent is placed in a crimper and the temperature elevated to facilitate greater compliance in the balloon material to allow material to extend between gaps in the stent struts. Additionally, balloon pressure is maintained while the stent is being crimped to increase stent retention to the balloon. After an initial pre-crimp, the stent is placed on the delivery balloon and allowed to slightly recoil under balloon pressure and while the stent has an elevated temperature. After this step, the stent is crimped onto the balloon while the balloon is pressurized. The stent is cycled through larger and smaller diameters. Additionally, balloon pressure may be supplied in bursts or held constant during these crimping steps. Further details of this process may be found in U.S. application Ser. No. 12/895,646 filed Sep. 30, 2010.

The art previously devised methods for retaining a balloon-expanded polymer scaffold on a delivery balloon. In one example, the scaffold is crimped to the delivery balloon at a temperature well below the polymer's TG. Then the scaffold, disposed between ends of the balloon, is thermally insulated from the balloon's ends. The ends of the balloon are then heated to about 185 degrees Fahrenheit to expand the diameter of the balloon material at its ends. The expanded balloon ends form raised edges abutting the scaffold ends to resist dislodgment of the scaffold from the balloon. In one example, this process provided a retention force of about 0.35 lb. for a Poly (L-lactide) (PLLA) scaffold crimped to a polymide-polyether block co-polymer (PEBAX) balloon. An example of this process is disclosed in U.S. Pat. No. 6,666,880.

Another example of a polymer scaffold crimping is found in U.S. Pat. No. 8,046,897, which has a common inventor with the present application. According to the '897 patent the balloon is inflated, or partially inflated before crimping. The scaffold is placed on the balloon. The crimping may take place at elevated temperatures, e.g., 30-50 degrees Celsius.

A film-headed crimper has been used to crimp stents to balloons. Referring to FIG. 7A, there is shown a perspective view of a crimping assembly 20 that includes three rolls 123, 124, 125 used to position a clean sheet of non-stick material between the crimping blades and the stent prior to crimping. For example, upper roll 125 holds the sheet secured to a backing sheet. The sheet is drawn from the backing sheet by a rotating mechanism (not shown) within the crimper head 20. A second sheet is dispensed from the mid roll 124. After crimping, the first and second (used) sheets are collected by the lower roll 123. As an alternative to rollers dispensing a non-stick sheet, a stent may be covered in a thin, compliant protective sheath before crimping.

FIG. 7B illustrates the positioning the first sheet 125*a* and second sheet 124*a* relative to the wedges 22 and a stent 100 within the aperture of the crimping assembly 20. As illustrated each of the two sheets are passed between two blades 22 on opposite sides of the stent 100 and a tension T1 and T2 applied to gather up excess sheet material as the iris of the crimping assembly is reduced in size via the converging blades 22.

The dispensed sheets of non-stick material (or protective sheath) are used to avoid buildup of coating material on the crimper blades for stents coated with a therapeutic agent. The sheets 125a, 124a are replaced by a new sheet after each crimping sequence. By advancing a clean sheet after each crimp, accumulation of contaminating coating material from previously crimped stents is avoided. By using replaceable sheets, stents having different drug coatings can be crimped using the same crimping assembly without risk of contamination or buildup of coating material from prior stent crimping.

There is a continuing need to improve upon methods for crimping a medical device and, in particular, a polymer scaffold to a delivery balloon in order to improve upon the uniformity of deployment of a polymer scaffold from the balloon, to increase the retention force between scaffold and balloon, and to obtain a minimal crossing profile for delivery of the scaffold to a target site.

SUMMARY OF THE INVENTION

The invention provides methods for increasing uniformity of polymer scaffold expansion via uniform scaffold crimping and improved balloon folding within the crimped scaffold to avoid the potential formation of broken struts, while maintaining or improving upon scaffold-balloon retention.

A preferred use for the invention is crimping a coronary scaffold to a delivery balloon. It has been demonstrated that the retention force of a crimped polymer scaffold on a delivery balloon may be increased by a crimping process that includes crimping the scaffold to the balloon while the balloon is pressurized; that is, the balloon is pressurized at the same time as the scaffold's outer diameter is being reduced by crimper blades. Additional features of such a crimping process include heating the scaffold to a temperature close to the glass transition temperature (TG) of the polymer material and applying balloon pressure during dwell periods (i.e., balloon pressure is applied when the scaffold diameter is held constant).

For a balloon-expanded polymer scaffold it has been found that processes for crimping the scaffold to the balloon, in order to ensure safe delivery to an implant site, expansion and implantation of an intact scaffold can be improved. In particular, it was found that certain modifications to crimping processes may better ensure that all four of the following objectives are met:

Structural integrity: avoiding damage to the scaffold's structural integrity when the scaffold is crimped to the balloon, or expanded by the balloon.
Safe delivery to an implant site: avoiding dislodgement or separation of the scaffold from the balloon during transit to an implant site and having a small crossing profile for the catheter.
Uniformity of expansion: avoiding non-uniform expansion of scaffold rings, which can lead to structural failure and/or reduced fatigue life.
Avoidance of balloon overstretch: monitoring of balloon pressure in relation to decreasing scaffold size to avoid excessive strain or possible pin-hole leaks in the balloon and without compromising the three prior needs.

Regarding the uniformity of expansion requirement, it has been recently found that earlier crimping processes, while satisfying the other two requirements, have not consistently expanded in a uniform manner when the balloon is expanded. As a consequence, ring struts and/or cell structures, which provide radial strength and stiffness for the scaffold, inherit an un-even distribution of stresses and strains. Over-expanded cells are called upon to sustain higher-than-normal stresses and strains while neighboring under-expanded cells are underutilized. The balloon-induced stresses and strains associated with over-expanded cells can exceed the material's ultimate stress and strain level at deployment, which might potentially result in crack formation, fracture or a reduced fatigue life or fracture toughness, in which case fracture can occur immediately, after a few days, or weeks after implantation.

In this invention, a crimping process includes balloon pressurization at relatively high pressures, prior to crimping, to allow substantially all of the pre-arranged folds of the balloon to be removed. While the balloon has this inflated state, the scaffold is then crimped to the balloon until the scaffold diameter has been reduced in size to about 50% (or more). In some embodiments, rather than about 50% the reduction is between 40-60%, between 50-60%, at most 50%, approximately 50%, or between 45-55%. After an about 50% (or more) reduction balloon pressure is relieved to avoid damage to the balloon and to achieve a small crossing profile.

For a balloon-expanded polymer scaffold, the outer diameter (OD) of a catheter's balloon ("Balloon A") may be smaller than the ID of the non-crimped scaffold, even when Balloon A is fully or even over inflated. In these cases, one may achieve a more uniform scaffold crimp by first partially or pre-crimping the scaffold using another balloon having a larger inflated or over inflated diameter than Balloon A. This other balloon ("Balloon B") has an over or fully inflated OD the same as or larger than the inner diameter (ID) of the non-crimped scaffold. Balloon B is used to offer support for the scaffold during a pre-crimp when the scaffold diameter is larger than Balloon A. Once the ID of the scaffold is crimped down to a size the same as Balloon A (it is understood that "the same size as" means not precisely equal sizes, but a range of sizes sufficiently close that they can be considered equal to each other for purposes of providing support during crimping), this pre-crimp step is finished and Balloon B is removed. Then the uniformly pre-crimped scaffold is placed onto the pre-inflated Balloon A. After a balloon-scaffold alignment check, the scaffold is returned to the crimper, where it is crimped down to a final crimp diameter on Balloon A.

According to a preferred embodiment, to achieve the most uniform scaffold crimping and balloon folding, which translates to more uniform scaffold expansion, the catheter's balloon (i.e., Balloon A) is fully inflated or over inflated (e.g., for a 3.0 mm semi-compliant PEBAX balloon 50 to 100 psi) and held in that state long enough, e.g., more than 10 seconds, to erase any pre-arranged folds. Balloon A is pressurized consistently during the whole crimping process at relatively medium pressure (e.g. 50 to 70 psi for a 3.0 mm semi-compliant PEBAX balloon).

Further, in accordance with this preferred embodiment, to achieve the lowest possible crossing profile and prevent balloon overstretch and/or formation of pinholes, it is found that the balloon pressure should be released when the scaffold diameter is still relatively large (e.g., more than 50% of the non-crimped scaffold). If the pressure is released too late, too much balloon material can become trapped among struts of the scaffold, which can not only result in a larger crossing profile, but also can overstretch and create pin holes in the balloon. Additionally, it is also preferred to begin to reduce pressure during a dwell period just prior to deflating the balloon (e.g., from 70 psi to 50 psi or lower). For the preferred embodiment, it was found that with the foregoing type of control of the crimping process a more effective balloon-scaffold engagement results; that is, one can achieve a better balance among achieving a low crossing profile, high scaffold-balloon retention force and uniform scaffold expansion, while avoiding damage to the balloon material. According to another embodiment, the crimping steps may include only 1, or only 3, or at most three dwell periods between an initial diameter reduction and final diameter reduction.

In the preferred embodiments methods of the invention are practiced using a polymeric scaffold. However, it is contemplated that the methods of invention may also be useful for addressing similar needs that can arise for other types of medical devices, such as metallic stents. For example, the methods for increasing the uniformity of deployment may be useful in addressing a need for greater uniformity for a balloon expandable stent made from a metal, metal alloy, bio-erodible metal or metal alloy or including a metal in the material used to make the stent.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

BRIEF DESCRIPTION OF THE DRAWINGS

FIGS. 8A-8C are photographs of the cross-section of a scaffold having a pre-crimp pattern as shown in FIG. 6 when crimped to a balloon of a balloon catheter. FIG. 8A shows the cross-section shape of balloon folds near the distal end of the balloon. FIG. 8B shows the cross-section shape of balloon folds near the middle of the balloon. FIG. 8C shows the cross-section shape of balloon folds near the proximal end of the balloon. The crimped scaffold and balloon of FIGS. 8A-8C was obtained using the '225 application process.

FIG. 9 is a photograph showing a scaffold having a pattern similar to that shown in FIG. 6 after balloon expansion. The scaffold shown in FIG. 10 was expanded using the '225 application process. As shown in this photograph, the scaffold exhibits a non-uniform expansion and there are fractures in the rings of the scaffold.

FIGS. 10A-10C are photographs of the cross-section of a scaffold having a pre-crimp pattern as shown in FIG. 6 when crimped to a balloon of a balloon catheter using a process according to the disclosure. FIG. 10A shows the cross-section shape of balloon folds near the distal end of the balloon. FIG. 10B shows the cross-section shape of balloon folds near the middle of the balloon. FIG. 10C shows the cross-section shape of balloon folds near the proximal end of the balloon. The crimped scaffold and balloon of FIGS. 10A-10C was obtained using the process of FIGS. 3A-3B.

FIG. 11 is a photograph showing a scaffold having a pattern similar to that shown in FIG. 6 after balloon expansion. The scaffold shown in this picture was expanded using the process of FIGS. 3A-3B. As shown in this photograph, the scaffold exhibits a more uniform expansion and there are no fractures in the rings of the scaffold.

DETAILED DESCRIPTION OF EMBODIMENTS

Figure 1A:
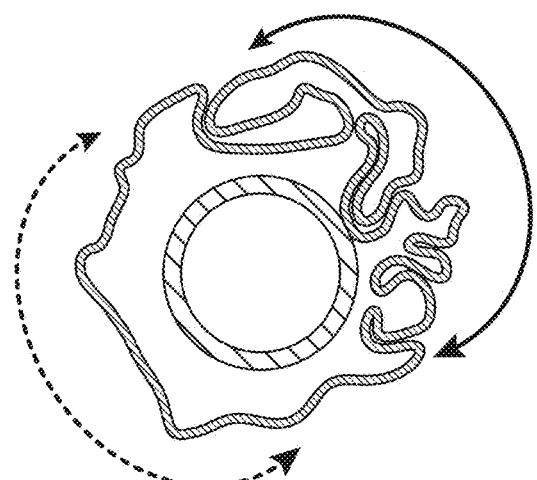
FIG. 1A shows an arrangement of balloon folds about a catheter shaft and near a distal end of a balloon after completion of the crimping process of FIGS. 1A-1B (crimped scaffold not shown).

The "glass transition temperature," TG, is the temperature at which the amorphous domains of a polymer generally change from a brittle, vitreous state to a solid deformable or ductile state at atmospheric pressure. In other words, the TG corresponds to the temperature where the onset of noticeable segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. TG of a given polymer can be dependent on the heating rate and can be influenced by the thermal history of the polymer. Furthermore, the chemical structure of the polymer heavily influences the glass transition by affecting mobility.

Crimping processes according to the disclosure crimp a scaffold to a fully inflated balloon. Thus, for a "3.0 mm balloon" (i.e., a balloon having a 3.0 mm rated inflated diameter) the term "fully inflated" means the balloon has an outer diameter of 3.0 mm when inflated. In a preferred embodiment a PEBAX, three-pleated semi-compliant balloon is used, which is rated to have a fully inflated state at approximately 70 psi. The pressure required to fully inflate a balloon depends on the balloon.

As explained in Applicants' co-pending U.S. application Ser. No. 13/473,031 filed May 16, 2012 non-compliant balloons are formed to have pleats or wings that open when pressure is supplied to the balloon. A process of forming such wings or pleats or folds (hereinafter "folds") is a common practice for semi- or non-compliant balloons. Examples of these types of balloons are described in U.S. Pat. Nos. 5,556,383, 6,488,688 and U.S. Pub. No. 2005/0244533. The pleats are formed by folds made in the balloon. The balloon material is folded according to a particular pattern or design intended to achieve an objective, e.g., a minimum profile. The folding is undertaken in an orderly manner either by hand or by a machine process, e.g., U.S. Pub. No. 2005/0244533. The balloon is typically heat set to hold the pleats in place, thereby forming pre-made or pre-set pleats.

For non-compliant balloons, which use material that is essentially non-elastic within the balloon operating ranges, the balloon inflates when pleats have unfolded. As such, non-compliant balloons sometimes have several tightly wound layers of prearranged folded balloon material when in the collapsed configuration in order to achieve a minimum profile or diameter for the balloon. Balloon pleats may be folded in a spiral or accordion like fashion, each approach to achieve a specific objective, e.g., low profile or reduced manufacturing complexity or quality control. Once folded, the balloon is heat set so that the balloon pleats are maintained in a tightly wound configuration about a catheter shaft. The heat set can be such that if the balloon pressure is increased enough to unfold the pleats, and then the balloon pressure is reduced back to, or below atmospheric; the balloon will take the same shape as it had prior to inflation. Above a certain inflation amount, the pleats can become completely or partially undone (so that when the inflation pressure is removed the folds do not return to their original heat-set pattern) as a scaffold interferes with the partially opened pleats.

The balloon inflation pressure for crimping according to the disclosure may be expressed as a percentage of the nominal inflation pressure for the balloon, e.g., 4 atmospheres (atm) for a 3.0 mm semi-compliant PEBAX balloon. Thus, for the inflation pressure 20-70 psi in the examples and a 7 atm nominal inflation pressure the crimping balloon pressure would correspond to about 20% to about 80% of the nominal inflation pressure for the balloon. And for the balloon having an 18 atm upper or over-inflated pressure (about 3.5 mm for a 3.0 mm nominally inflated balloon) the crimping balloon pressure would correspond to about 10% to about 30% of the upper or over-inflated balloon pressure. For the immediately preceding dwell stage according to the embodiments, e.g., Stage IV in FIG. 3A, the pressure may be decreased down to at least 1 atm before the balloon pressure is completely removed at the final diameter reduction step.

Poly(lactide-co-glycolide) (PLGA) and Poly (L-lactide) (PLLA) are examples of a class of semi-crystalline polymers that may be used to form the scaffolds described herein. PLLA is a homopolymer and PLGA is a co-polymer. The percentage of glycolide (GA) in a scaffold constructed of PLGA may vary, which can influence the lower range of TG. For example, the percentage of GA in the matrix material may vary between 0-15%. For PLLA, the onset of glass transition occurs at about 55 degrees Celsius. With an increase of GA from about 0% to 15% the lower range for TG for PLGA can be correspondingly lower by about 5 degrees Celsius. For PLGA having % GA of about 5% the temperature ranges for crimping may be between about 46 to 53 degrees Celsius. For PLGA having % GA of about 15% the temperature ranges for crimping are about 43 to 50 degrees Celsius.

In one embodiment, a tube is formed by an extrusion of PLLA. The tube forming process described in US Pub. No. 2010/00025894 may be used to form this tube. The finished, solidified polymeric tube of PLLA may then be deformed in radial and axial directions by a blow molding process wherein deformation occurs progressively at a predetermined longitudinal speed along the longitudinal axis of the tube. For example, blow molding can be performed as described in U.S. Publication No. 2009/0001633. This biaxial deformation, after the tube is formed, can produce noticeable improvement in the mechanical properties of the scaffold structural members cut from the tube without this expansion. The degree of radial expansion that the polymer tube undergoes characterizes the degree of induced circumferential molecular or crystal orientation. In a preferred embodiment, the radial expansion ratio or RE ratio is about 450% of the starting tube's inner diameter and the axial expansion ratio or AE ratio is about 150% of the starting tube's length. The ratios RA and AE are defined in U.S. Pub. No. 2010/00025894.

A scaffold's outer diameter (made according to the foregoing processes) may be designated by where it is expected to be used, e.g., a specific location or area in the body. The outer diameter, however, is usually only an approximation of what will be needed during the procedure. For instance, there may be extensive calcification that breaks down once a therapeutic agent takes effect, which can cause the scaffold to dislodge in the vessel. Further, since a vessel wall cannot be assumed as circular in cross-section, and its actual size only an approximation, a physician can choose to over-extend the scaffold to ensure it stays in place. For this reason, it is sometimes preferred to use a tube with a diameter larger than the expected deployed diameter of the scaffold.

As discussed earlier, fabrication of a scaffold presents challenges that are not present in metallic stents. One challenge, in particular, is the fabrication of a scaffold, which means the load bearing network of struts including connectors linking ring elements or members that provide the radial strength and stiffness needed to support a lumen. In particular, there exists an ongoing challenge in fabricating a scaffold that is capable of undergoing a significant degree of plastic deformation without loss of strength, e.g., cracks or fracture of struts. In one embodiment the ratio of deployed to fully crimped diameter is about 2.5. In this embodiment, the crimped diameter corresponds to an outer diameter that is only about 40% of the starting diameter. Hence, when deployed the drug eluting scaffold is expected to increase in size at least to about 2.5 times its crimped diameter size.

In one particular example, a scaffold is formed from a bi-axially expanded tube having an outer diameter of 3.5 mm, which approximately corresponds to a deployed diameter (the scaffold may be safely expanded up to 4.0 mm within a lumen). The iris of the crimping mechanism reaches a diameter of 0.044 in, which is maintained for a 170 sec dwell period (i.e., scaffold held at 0.044 in outer diameter within crimping mechanism). When later removed from the crimper, the scaffold will recoil despite there being a restraining sheath placed over the scaffold immediately after the scaffold is removed from the crimper. The scaffold and sheath are then subjected to radiation sterilization. At the point of use, i.e., at the point in time when a medical specialist removes the restraining sheath, the scaffold has an outer diameter of about 0.052 in (1.32 mm), or about 35-40% of the starting tube diameter of 3.5 mm. When in the crimping mechanism the scaffold reaches about 30-35% of the starting tube size.

An additional challenge faced with the scaffold is the ability of the scaffold to be crimped to the balloon so that an adequate retention force is established between the scaffold and balloon. A "retention force" for a scaffold crimped to a balloon means the maximum force applied to the scaffold along the direction of travel through a vessel that the scaffold-balloon is able to resist before dislodging the scaffold from the balloon. The retention force for a scaffold on a balloon is set by a crimping process, whereby the scaffold is plastically deformed onto the balloon surface to form a fit that resists dislodgment of the scaffold from the balloon. Factors affecting the retention of a scaffold on a balloon are many. They include the extent of surface-to-surface contact between the balloon and scaffold, the coefficient of friction of the balloon and scaffold surfaces, and the degree of protrusion or extension of balloon material between struts of the scaffold. As such, the magnitude of a pull off or retention force for a scaffold generally varies with its length. The shorter scaffold, therefore, is more likely to dislodge from the balloon as the catheter is pushed through tortuous anatomy than a longer scaffold where the same crimping process is used for both the longer and shorter scaffolds.

For a metal stent there are a wide variety of methods known for improving the retention force of a stent on a balloon via modification of one or more of the foregoing properties; however, many are not suitable or of limited usefulness for a scaffold, due to differences in mechanical characteristics of a scaffold verses a metal stent, as discussed earlier. Most notable among these differences is brittleness of polymer material suitable for balloon-expanded scaffold fabrication, verses that of a metal stent, and the sensitivity of the polymer material to heat. Whereas a metal stent may be deformed sufficiently to obtain a desired retention force, the range of deformation available to a polymer scaffold, while avoiding cracking or fracture-related problems, by comparison, is quite limited. The application of heat has been shown as effective for increasing retention forces for metal stents. However, the heat levels used can cause detrimental effects to the polymer material since they tend to correspond to temperatures well within, or above the TG of the material. For this reason, known heat methods for increasing retention forces for metal stents tend to be viewed as inappropriate for increasing a retention force between a scaffold and balloon.

It has been more of a challenge to achieve high retention forces for a crimped polymer scaffold, as compared to a crimped metal stent, for basically two reasons. First, there is less space available between struts in a crimped state, which prevents balloon material from extending between struts. As a result, there is less abutment or interference between struts and balloon material, which interference/abutment has previously been relied upon to increase the retention force of a metal stent on a balloon. This condition is a result of the need to fabricate wider and thicker struts for the scaffold, as compared to a metal stent, so as to provide adequate, deployed radial strength. Additionally, metal stents may be cut from a tube closer to the crimp diameter whereas a polymer scaffold may be cut from a tube at about the fully expanded diameter, which further reduces the space between struts in the crimped configuration. Second, a polymer is more sensitive to temperature ranges that have previously been used to increase retention to a balloon. Heating of a scaffold to within, or above TG induces significant changes in the molecular orientation of the polymer material that result in loss of strength when the scaffold is plastically deformed to its deployed diameter.

U.S. Pat. No. 8,261,423 ('423 patent) discusses a study that was conducted to investigate the effects on retention forces for crimped scaffolds. Principally, this study identified a temperature range relative to a TG of the scaffold material that improved retention forces without detrimentally affecting scaffold mechanical properties when deployed to support a vessel. For PLLA it was found that modifying the pressure and hold time of the scaffold for crimping temperatures of between about 40° and 55° C. improved the scaffold retention, with about 45-51° C. and about 48° C. being preferred temperatures for a PLLA scaffold. Additionally, the '423 patent found that retention forces could be improved if the scaffold were crimped down to an intermediate diameter and then the balloon is deflated then re-inflated, followed by crimping the scaffold down to a final crimp diameter. The '423 patent also contemplates similar results for PLGA, if TG for this material is taken into consideration and assuming other characteristics of the process and scaffold pattern. For PLGA having % GA of about 5% the temperature ranges for crimping may be between about 46 to 53 degrees Celsius. For PLGA having % GA of about 15% the temperature ranges for crimping are about 43 to 50 degrees Celsius.

FIG. 1 of the '423 patent shows a flow for a crimping process for a 3.0 mm (0.118 in) scaffold that is crimped to a final crimp diameter of 0.044 in. The diameter reduction from 0.118 in to 0.044 in includes three intermediate crimping diameters of 0.083 in, 0.063 in and 0.07 in, following a "pre-crimp" procedure in which the PLLA scaffold temperature is raised to a temperature of about 48° C. When the scaffold has attained the intermediate crimp diameters, the crimper jaws are held at the crimping diameter for a dwell period of 30 sec, 15 sec and 10 sec, respectively. After the final crimp diameter has been obtained, the crimp jaws are held at the final crimp diameter for about 200 sec. The delivery balloon, i.e., a PEBAX balloon, is inflated to a pressure of 17 psi for the dwell period 30, 15 and 10 second dwell periods. The dwell periods for the intermediate crimping stages are included in the process to allow for stress relaxation in the polymer material before decreasing the scaffold diameter further. Before the crimper iris is reduced by actuation of the crimper jaws, the balloon is deflated. Thus, in the example from the '423 patent whenever the scaffold diameter is decreased, the balloon is not inflated.

Notwithstanding improved results in stent retention when practicing inventions described in the '423 patent, it is desirable to further increase a scaffold retention force. For example, for a coronary scaffold it is desirable to have a balloon-scaffold retention force (i.e., force required to pull scaffold off balloon) of at least 0.7 lbs and preferably over 1.0 lbs.

Processes have been previously proposed for achieving a high retention force, maintaining the structural integrity of a crimped polymer scaffold and improving uniformity of deployment form the balloon. One such process is described in co-pending application Ser. No. 13/438,211 (the '211 application) having a common assignee as this application.

Figure 3A:
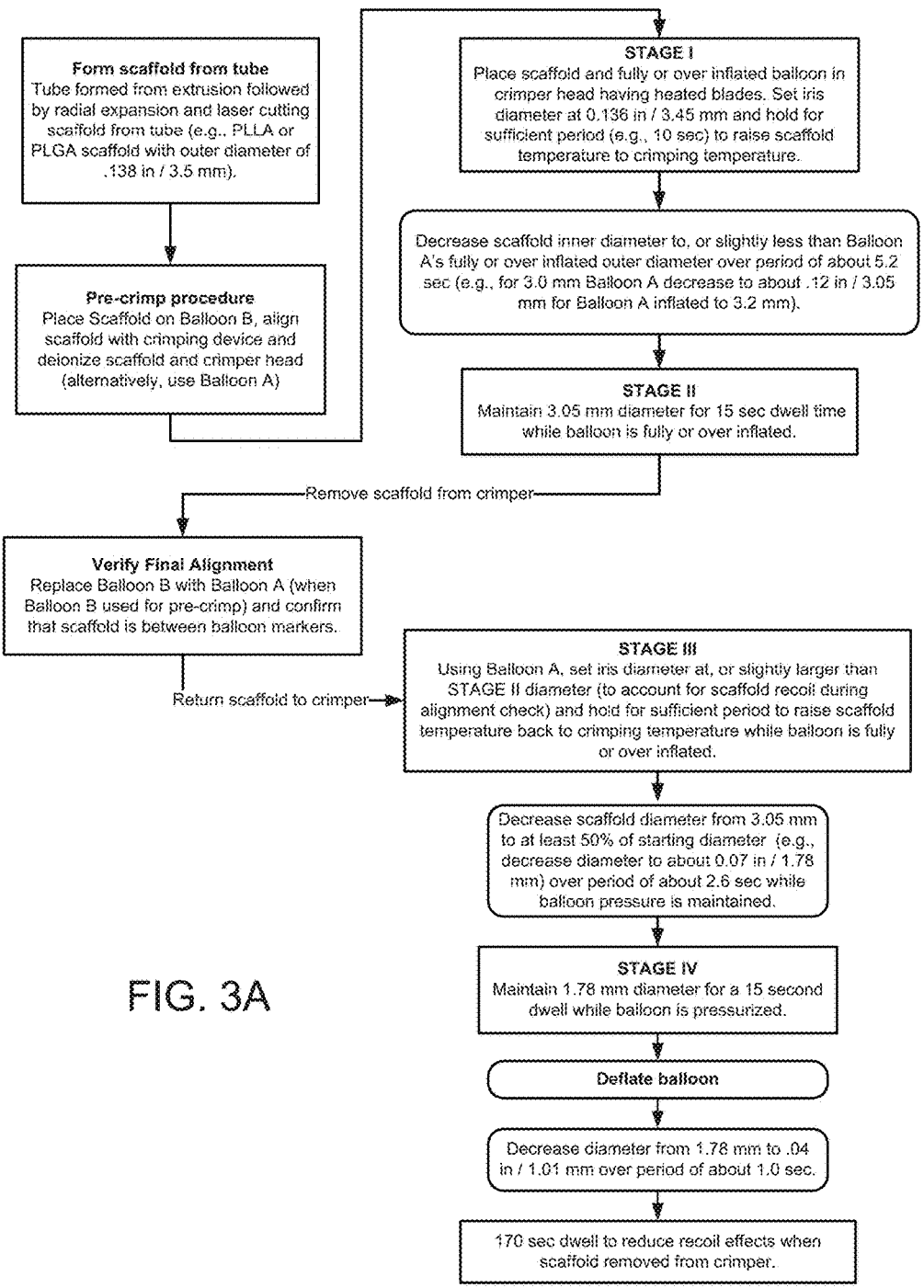
FIG. 3A is an example of a flow process for crimping a polymer scaffold to a balloon according to the disclosure. In this example, a Balloon A and a Balloon B are used to crimp the scaffold. The Balloon A is the balloon of the delivery device for delivery of the scaffold to a vessel site. The Balloon B is a secondary balloon used for a pre-crimp process when the initial scaffold diameter is greater than the fully or over-inflated Balloon A.
Figure 3B:
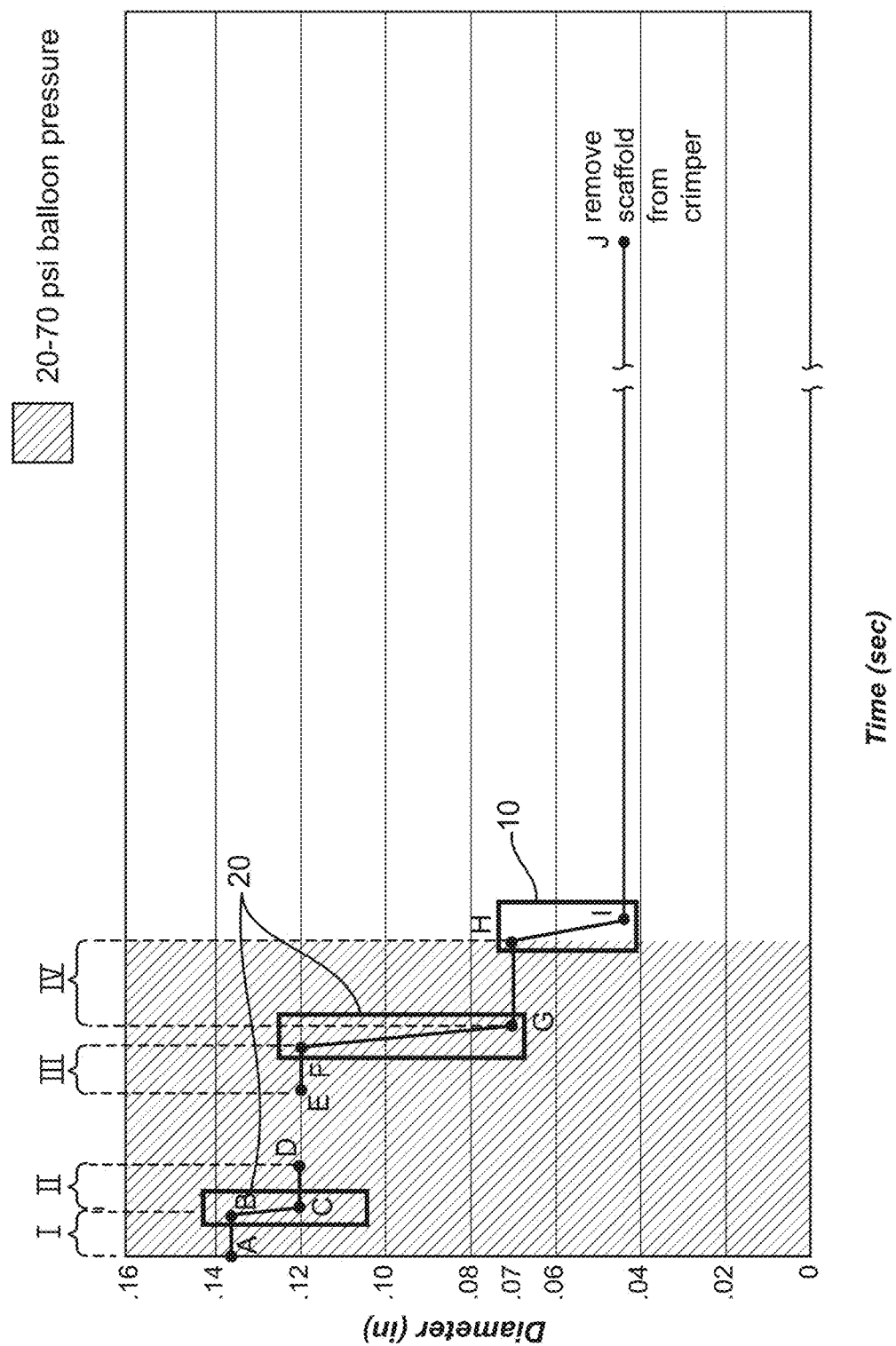
FIG. 3B shows the crimping portion of the FIG. 3A flow process in graphical form, plotting scaffold diameter vs. time and indicating the balloon pressure supplied during steps of the crimping process.

FIGS. 3A-3B describe an example of a flow process and graph, respectively, of a crimping method for a 3.5 mm diameter and 18 mm length. The method is described in terms of a series of five "stages" with diameter reduction steps between stages. Each "stage" refers to a period where the crimper jaws are maintained at a constant diameter for a dwell period. The scaffold diameter is held constant during these periods. The boxes 20 and 10 in the graph is identifying times when the iris diameter is being reduced.

Figure 4A:
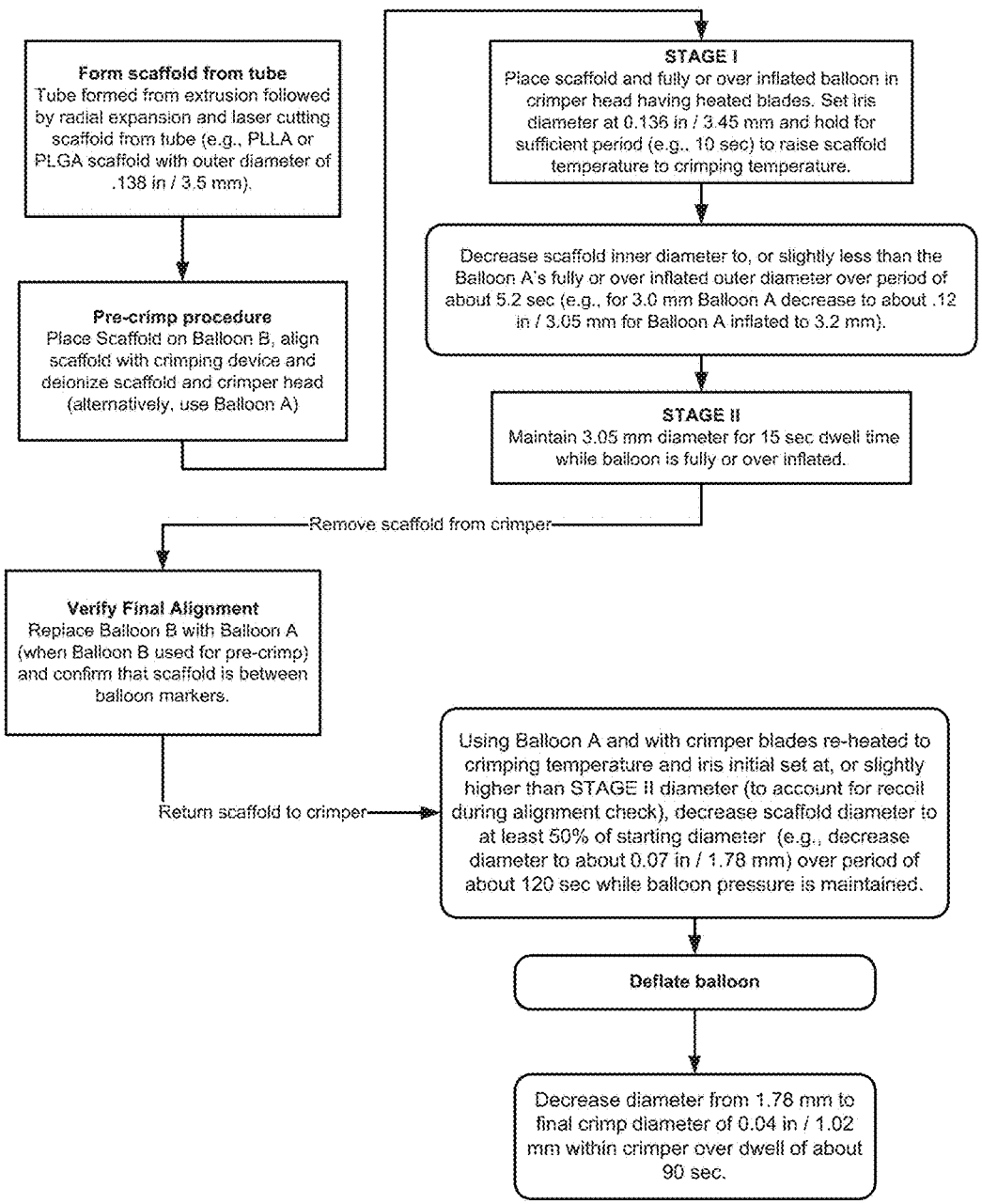
FIG. 4A is another example of a flow process for crimping a polymer scaffold to a balloon according to the disclosure. In this example, a Balloon A and a Balloon B are used to crimp the scaffold. The Balloon A is the balloon of the delivery device for delivery of the scaffold to a vessel site. The Balloon B is a secondary balloon used for a pre-crimp process when the initial scaffold diameter is greater than the fully or over-inflated Balloon A.

For crimping steps preceding and following the "verify final alignment" step in FIGS. 3A-3B, where the scaffold and balloon are removed from the crimper to check alignment, the balloon is fully inflated for substantially the entire period that the scaffold resides within the crimper (i.e., points A-H in FIG. 3B, although in one embodiment the balloon pressure is decreased or allowed to slowly decrease to a lower pressure at point G, or gradually decrease to a lower pressure between points G and H in FIG. 3B). As shown in FIGS. 3A and 4A, a Balloon B may be used for the steps leading up to the "verify final alignment" step. Balloon B is then replaced by Balloon A. Some of the advantages of inflating a balloon when crimping to achieve this result are explained in U.S. application Ser. No. 12/861,719 filed Aug. 23, 2010 (US20120042501) (the '719 application).

As mentioned earlier, a polymer scaffold, and in particular a misaligned polymer scaffold is more susceptible to damage within a crimper than a corresponding metal stent. A polymer scaffold that has even a "slight" misalignment within the crimper has a far greater chance of becoming damaged than a metal stent. Of course, the need to avoid twisting or bending in struts of metal stents when in a crimper is known. However, unlike metal stents, which are far more tolerant of local irregular or non-uniform forces acting on struts through blade edges, polymer struts are more easily distorted when the crimping forces are non-uniformly applied. Due to the proximity of struts to each other (as required since thicker and wider struts are needed to provide equivalent stiffness to a metal stent and there is sometimes a greater diameter reduction needed during crimping), there is a greater chance of abutting struts which leads to out of plane twisting and overlapping scaffold structure in the crimped state. The effects of irregular or non-uniform crimping forces on a polymer scaffold are therefore more severe than in the case of a metal stent. The differences are most clearly evident in the instances of cracking and/or fracture in deployed polymer scaffolds that show irregular twisting or bending.

More local support for individual struts is believed to correct or account for struts that may be predisposed to twist or overlap with adjacent struts. In essence, balloon pressure is believed to apply a beneficial correcting force on the luminal side of struts, which can serve to limit a strut's potential to overlap or twist further as crimper blades are applied in subsequent steps.

As discussed in the '211 application, when a scaffold is crimped down from a larger diameter, there is little stabilizing support available since its diameter is much larger than the deflated balloon upon which the scaffold sits. As such, any initial non-uniform applied crimping force, or misalignment, e.g., due to a residual static charge on the polymer surface, can initiate irregular bending that becomes more pronounced when the scaffold diameter is reduced further. Friction between the blades and the scaffold surface, or residual static charge or static charge buildup induced by sliding polymer surfaces are also suspect causes of this irregular deformation of the scaffold. When the balloon is inflated to support the scaffold from the interior, the irregular bending and twisting of struts seen at the final crimp diameter (when the scaffold is removed from the crimper) can be reduced substantially.

EXAMPLE 1

FIGS. 3A-3B illustrate steps associated with a first crimping process according to the disclosure. In this example there is a crimping process described for crimping a 3.5 mm scaffold to a 3.0 mm semi-compliant PEBAX balloon. FIG. 3B illustrates in graphical form the crimping portion of the FIG. 3A flow—a graph of scaffold diameter verses time with a balloon pressure of between about 20-70 psi (or 1 atm up to the fully or over-inflated balloon pressure) applied throughout substantially all of the crimping process. For example, the balloon pressure is maintained at 70 psi for steps A-G, then the pressure is allowed to decrease (or deflated) to 50 psi (or 1 atm) for the period G-H. Balloon pressure is removed at point H. No balloon pressure is used H-J for purposes of achieving a low crossing profile and avoiding damage to the balloon.

FIG. 3A (as well as FIG. 4A, discussed infra) indicate three possibilities for crimping, depending on need. First, there are two balloons used: Balloon A and Balloon B. balloon B is used for the pre-crimp step(s) and Balloon A (used with the delivery system) is used for the final crimp. Second, there is only one balloon used (Balloon A) for the entire crimp process including the verify alignment check. In this case, the scaffold inner diameter is larger than the fully or overinflated Balloon A. As such, during pre-crimp there may be shifting on the balloon. Third, there is only one balloon used (Balloon A) for the entire crimp process without a verify final alignment check. In this case, the balloon for the delivery system has a fully or overinflated state that is about equal to the inner diameter of the scaffold.

Stage I: The scaffold supported on the fully inflated balloon of the balloon-catheter is placed within the crimp head. The balloon when inflated and supporting the scaffold in this state has substantially all folds removed. In a preferred embodiment the catheter's balloon (i.e., the balloon used in the final product—a stent delivery system) is used for Stage I through Stage II. In other embodiments it may be preferred to use a second, larger balloon for Stage I and II (as explained in more detail below). The blades of the crimper are heated to raise the scaffold temperature to a crimping temperature. In the preferred embodiments the crimping temperature is between a lower end of the glass transition temperature for the polymer (TG-LOW) and 15 degrees Celsius below TG-LOW. In a particularly preferred embodiment the polymer of the scaffold is PLLA and the crimping temperature is about 48 degrees Celsius, or between about 43 and 54 degrees Celsius.

After the scaffold reaches the crimping temperature, the iris of the crimper closes to reduce the scaffold inner diameter (ID) to slightly less than the outer diameter (OD) of the fully or over inflated balloon (e.g., from 3.45 mm to about 3.05 mm for the PEBAX 3.0 mm semi compliant balloon inflated to a diameter of about 3.2 mm). In this example, Balloon B would be used for the diameter reduction down to the 3.0 mm balloon size, or the Balloon A size (e.g., the 3.0 mm balloon).

Stage II: The crimper jaws are held at the 3.05 mm diameter and maintained at this diameter for a second dwell period at the crimping temperature. After Stage II the scaffold has about 90% of its pre-crimp diameter.

The foregoing Steps I-II reduce the scaffold diameter down to the size of the fully inflated balloon of the stent delivery system (i.e., Balloon A). Since at the time of the initial alignment check (before any crimping) the scaffold inner diameter was larger than the balloon fully inflated diameter (e.g. the scaffold diameter is about 109%-116% of the fully inflated balloon diameter for a balloon with diameters of 3.0 mm to 3.2 mm, respectively) there is a possibility that the scaffold shifts longitudinally (relative to the balloon) while being crimped down to the balloon size. Given this possibility, the scaffold is removed from the crimper and its alignment on the balloon is checked relative to proximal and distal balloon markers.

"Verify final alignment" step: When the scaffold requires adjustment on the balloon, a technician makes manual adjustments to move the scaffold into position. It has been found difficult, however, to make these minor adjustments while the scaffold rests on the fully inflated balloon and has an inner diameter slightly less than the balloon's outer diameter. To address this need, the balloon pressure is slightly decreased, or the balloon temporarily deflated so that the re-alignment may be done more easily. When the scaffold is properly re-aligned between the balloon markers, the scaffold and fully inflated balloon are placed back into the crimper. With the scaffold inner diameter and balloon sizes now about equal the final crimping of the scaffold to the catheter's balloon can commence. To ensure no further longitudinal movement of the scaffold relative to the balloon, it is preferred to have the scaffold diameter be slightly less than the balloon fully inflated diameter prior to the start of Stage III. As noted above, where two balloons are used, Balloon B is replaced with Balloon A, alignment is done with respect to Balloon A and the scaffold is crimped down to the final diameter on Balloon A.

Stage III: The scaffold and balloon are returned to the crimper. The jaws are closed to a diameter about the same as, or slightly larger than in Stage II (to account for recoil occurring during the alignment check). The crimper jaws are held at this diameter for a third dwell time, which may be the time needed for the scaffold to return to the crimping temperature.

The iris diameter is then reduced to an ID corresponding to about, or slightly less than the OD for the balloon if the balloon were not pressurized and had randomly distributed folds. That is, the scaffold is crimped down to the approximate OD for the balloon if it were pressurized then deflated so that substantially all pre-made folds are replaced by random folds. For example, the iris diameter is reduced down to about 1.78 mm for the 3.5 mm scaffold. After this diameter reduction the scaffold OD is about 60% of its diameter at Stage III and about 50% of its starting, or pre-crimp OD.

Stage IV: After the scaffold OD is reduced to about 50% of its starting diameter, the crimper jaws are held at this diameter for a third dwell time. In a preferred embodiment balloon pressure is slightly decreased during this dwell. For example, for the 3.0 mm semi-compliant PEBAX balloon the pressure is decreased from 70 psi to 50 psi during the Stage IV dwell. This decrease is preferred to achieve a lower crossing profile and/or to protect balloon material from overstretch.

Following the Stage IV dwell period, the balloon is deflated or allowed to return to atmospheric pressure and the iris of the crimper is reduced down to a final crimp OD, e.g., 1.01 mm or about 30% of its pre-crimp OD. This balloon deflation may occur by opening the valve supplying the pressurized gas to the balloon while, or just before the iris diameter is reduced to the final crimp diameter.

The crimper jaws are then held at the final crimp diameter for about a 170 second dwell period. This final dwell period is intended to reduce the amount of scaffold recoil when the crimped scaffold is removed from the crimper. Immediately following the 170 second dwell the scaffold is removed and a retaining sheath is placed over the scaffold to further aid in reducing recoil. A leak test may be done after the final stage crimping.

It may be necessary to provide auxiliary pressure sources for a balloon in order to maintain a relatively constant pressure throughout the diameter reduction and dwell periods (as illustrated in the above example). Indeed, in one embodiment it was found that during diameter reduction there was a pressure drop in the balloon. To address this pressure drop, a secondary pressure source was used to maintain the same pressure during diameter reductions as during dwell periods.

The foregoing example of a preferred crimping process, which selectively pressurizes the balloon throughout the crimping steps, is expected to provide three benefits while minimizing any possible overstretching of the balloon. The first benefit is increased scaffold-balloon retention. By maintaining relatively high pressure in the balloon through most of the crimping steps, more balloon material should become disposed between struts of the scaffold since balloon material is being pressed more into the scaffold, than the case when crimping is done without balloon pressurization, or only after the scaffold is substantially reduced in diameter. Additionally, it is expected that by substantially removing folds before any diameter reduction, the balloon material becomes more compliant. As such, more balloon material is able extend between struts, rather than being pressed between the scaffold and catheter shaft when the scaffold is being crimped.

Figure 1B:
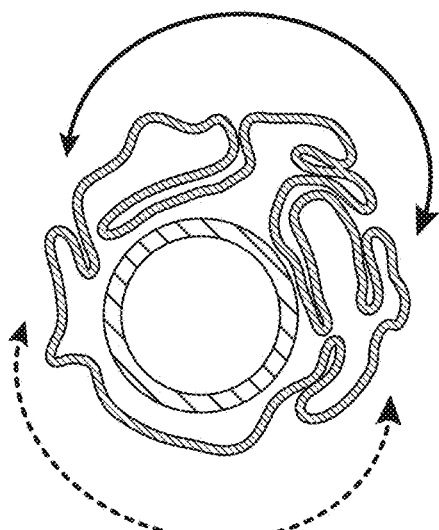
FIG. 1B shows an arrangement of balloon folds about a catheter shaft (crimped scaffold not shown) and near the middle of the balloon when using a crimping process as described in U.S. application Ser. No. 13/089,225 ('225 application).
Figure 1C:
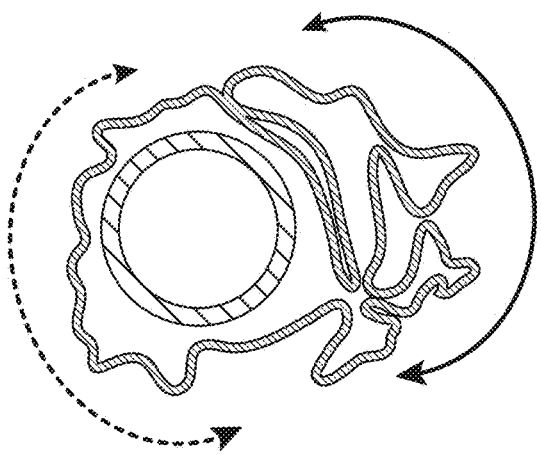
FIG. 1C shows an arrangement of balloon folds about a catheter shaft and near the proximal end of the balloon when using the '225 application crimping process.

The second benefit of balloon pressurization is more uniform expansion of the crimped scaffold when the balloon is expanded. When the balloon is inflated from the beginning, before any crimping takes place and when there is the greatest space available for the balloon to unfold within the mounted scaffold, balloon material become more uniformly disposed about the circumference of the catheter shaft after crimping. In a preferred embodiment the balloon is fully inflated and held at this inflated state for at least 10 seconds before any crimping to ensure all pre-made folds are removed. If the balloon is only partially expanded, as in the case where the balloon is inflated after the scaffold has been partially crimped (thereby leaving less space available for the balloon to fully unfold), fold lines or balloon memory not removed by balloon pressure, it is believed that the presence of folds or partial folds causes balloon material to shift or displace during crimping, thereby resulting in a more non-uniform distribution of balloon material about the circumference of the catheter shaft after crimping. This type of behavior is depicted in FIGS. 1A-1C.

The third benefit is avoidance of out of plane twisting or overlapping scaffold struts, which can result in loss of strength, cracks or fracture in struts. As discussed earlier, support of the scaffold within crimper with an inflated balloon is believed to counteract or minimize any tendency for struts to move out of alignment.

The foregoing benefits may be achieved without risk that balloon material will be excessively stretched during the crimping process when balloon pressure is selectively controlled. Referring to FIG. 3B, the pressure range provided is 20-70 psi. The upper end of this pressure range forms the fully inflated balloon in the case of the balloon used in the example and may be maintained for the first three stages. Balloon pressure reduction to 50 and 20 psi for Stage IV follows. It was found through several tests that maintaining a constant, and consistent fully inflated balloon pressure up until the beginning of stage IV or after the crimped scaffold had reached about ½ of the original scaffold diameter, followed by a slight decrease in pressure, provided a good balance of stent retention, uniform expansion, low crossing profile, uniform crimping and avoidance of damage to balloon material.

Figure 5A:
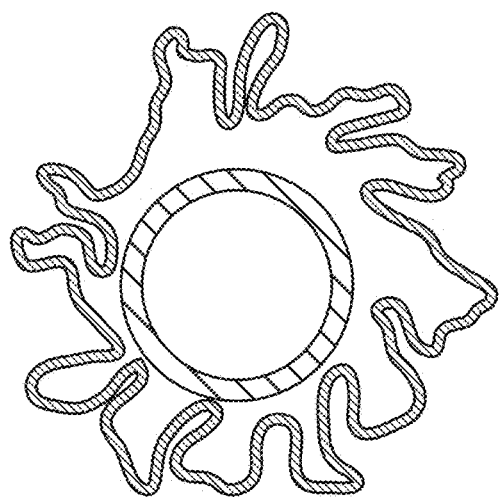
FIG. 5A shows an arrangement of balloon folds about a catheter shaft and near a distal end of a balloon after completion of the crimping process of FIGS. 3A-3B (crimped scaffold not shown).
Figure 5B:
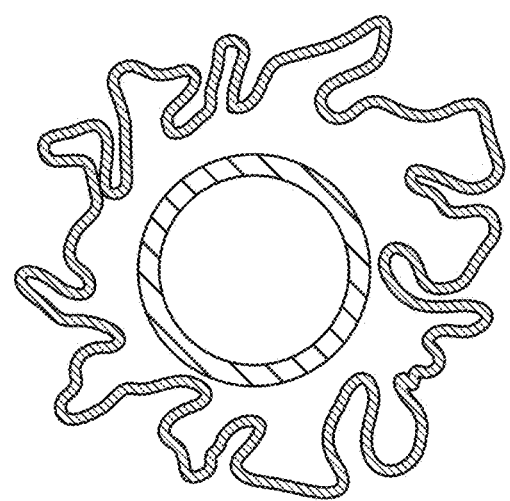
FIG. 5B shows an arrangement of balloon folds about a catheter shaft and near the middle of the balloon after completion of the crimping process of FIGS. 3A-3B (crimped scaffold not shown).
Figure 5C:
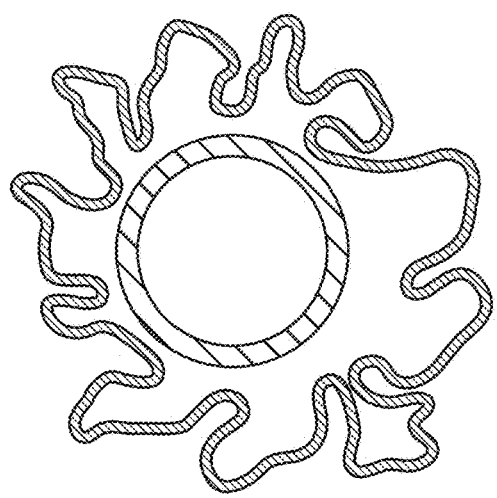
FIG. 5C shows an arrangement of balloon folds about a catheter shaft and near the proximal end of the balloon after completion of the crimping process of FIGS. 3A-3B (crimped scaffold not shown).

FIGS. 5A, 5B, and 5C are drawings intending to depict observed arrangements, or distributions of balloon folds when a scaffold is fully crimped (scaffold not shown) using the preferred process of FIGS. 3A-3B ((photographs of the cross-section of a scaffold crimped to a balloon, taken from the distal, middle and proximal portions of the balloon are provided in FIGS. 10A-10C). FIG. 5A shows the arrangement of balloon folds about the circumference of the catheter shaft nearer the distal end of the balloon. FIG. 5B shows the arrangement of balloon folds about the circumference of the catheter shaft nearer the middle of the balloon. And FIG. 5C shows the arrangement of balloon folds about the circumference of the catheter shaft nearer the proximal end of the balloon. As compared to the corresponding FIGS. 1A, 1B and 1C discussed earlier, FIGS. 5A-5C shown balloon material more evenly distributed about the circumference of the catheter shaft. It was found that when balloon material is arranged in a manner similar to that shown in FIGS. 5A-5C, there was less non-uniformity in the expanded scaffold and less instances of cracks or fractures in scaffold struts caused by over expansion.

Figure 12A:
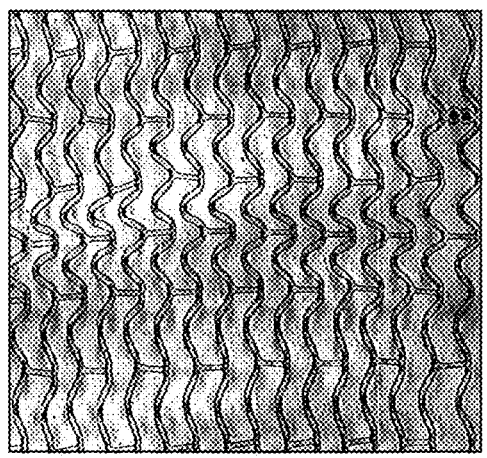
FIG. 12A is a FINESCAN image of a scaffold having a pattern similar to that shown in FIG. 6. The scaffold was crimped using the '225 application process. The scaffold was then expanded by inflation of the balloon. As shown in this image, the scaffold exhibits a non-uniform expansion.
Figure 12B:
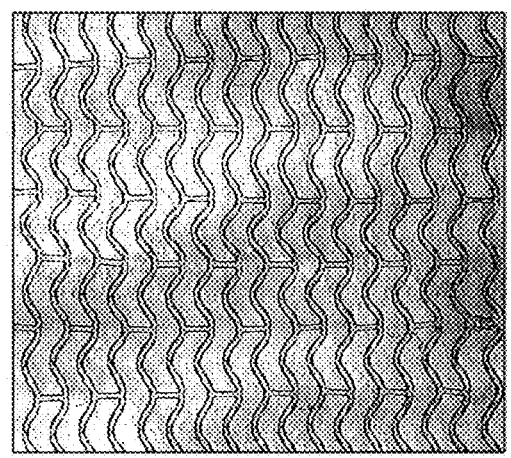
FIG. 12B is a FINESCAN image of a scaffold having a pattern similar to that shown in FIG. 6. The scaffold was crimped using the process of FIGS. 3A-3B. The scaffold was then expanded by inflation of the balloon. As shown in this image, the scaffold exhibits a more uniform expansion than the scaffold in FIG. 12A.

FIG. 12B shows a FINESCAN image of a scaffold expanded after being crimped using the process of FIGS. 3A-3B. FIG. 11 shows a perspective view of a scaffold expanded after crimping using this process. As can be appreciated by comparing these photographs to FIGS. 12A and 9, respectively, when crimped using the FIGS. 3A-3B process the scaffold expands more uniformly.

As noted earlier, there are three possibilities for crimping: use two balloons—Balloon A and Balloon B. Balloon B is used for the pre-crimp step (a) and Balloon A (used with the delivery system) is used for the final crimp. Second, there is only one balloon used (Balloon A) for the entire crimp process including the verify alignment check. In this case, the scaffold inner diameter is larger than the fully or overinflated Balloon A. As such, during pre-crimp there may be shifting on the balloon. Third, there is only one balloon used (Balloon A) for the entire crimp process without a verify final alignment check. In this case, the balloon for the delivery system has a fully overinflated state that is about equal to the inner diameter of the scaffold inner diameter. These different embodiments are described further, below.

In a first alternative embodiment a process is described by example in FIGS. 3A-3B and as described above, with the following exception. Two balloons are used—a sacrificial or secondary balloon (Balloon B) in addition to the catheter's balloon (Balloon A)—as opposed to only Balloon A as in the above example of a preferred embodiment. Balloon B is a balloon that has a larger nominally inflated balloon diameter than Balloon A, or is capable of being over inflated to a larger diameter than Balloon A. Balloon B is used for Stages I and II. Balloon B is selected to have a fully inflated diameter that is the same as, or slightly larger than the original inner diameter of the scaffold. One advantage of this alternative embodiment is that the scaffold is supported by a balloon throughout the crimping process (as opposed to the above example where Balloon A can provide little or no radial support for the scaffold since there is a gap at Stage I). After Stage II, the scaffold is removed from the crimper and Balloon B is replaced by Balloon A. Thereafter, the crimping process continues as described earlier.

In a second alternative embodiment a stent delivery system uses a balloon that can be inflated to a diameter equal to or larger than the original inner diameter of the scaffold (e.g., a 3.0 mm balloon that can be inflated to 3.5 mm). Alternatively, a medical device (e.g., a scaffold or other type of balloon-expandable medical device such as a metal stent) is not made to a have an inner diameter larger than the nominal or average vessel size where it is intended. In either case, the catheter's delivery balloon is capable of providing good radial support for the medical device prior to any crimping.

This second alternative embodiment is described by example in FIGS. 3A-3B and as described above with the following exceptions. First, the "form scaffold from tube" may be form stent from metal alloy tube and the pre-crimp procedure may not need a deionization step, for example. Second, the "Verify Final Alignment" step may be removed since the medical device is being supported by the balloon throughout the crimping process. Thus, unlike the original example above, since the fully inflated balloon fits snugly against the medical device throughout the process, it is reasonable to expect that the medical device will not shift out of alignment during crimping.

EXAMPLE 2

Figure 4B:
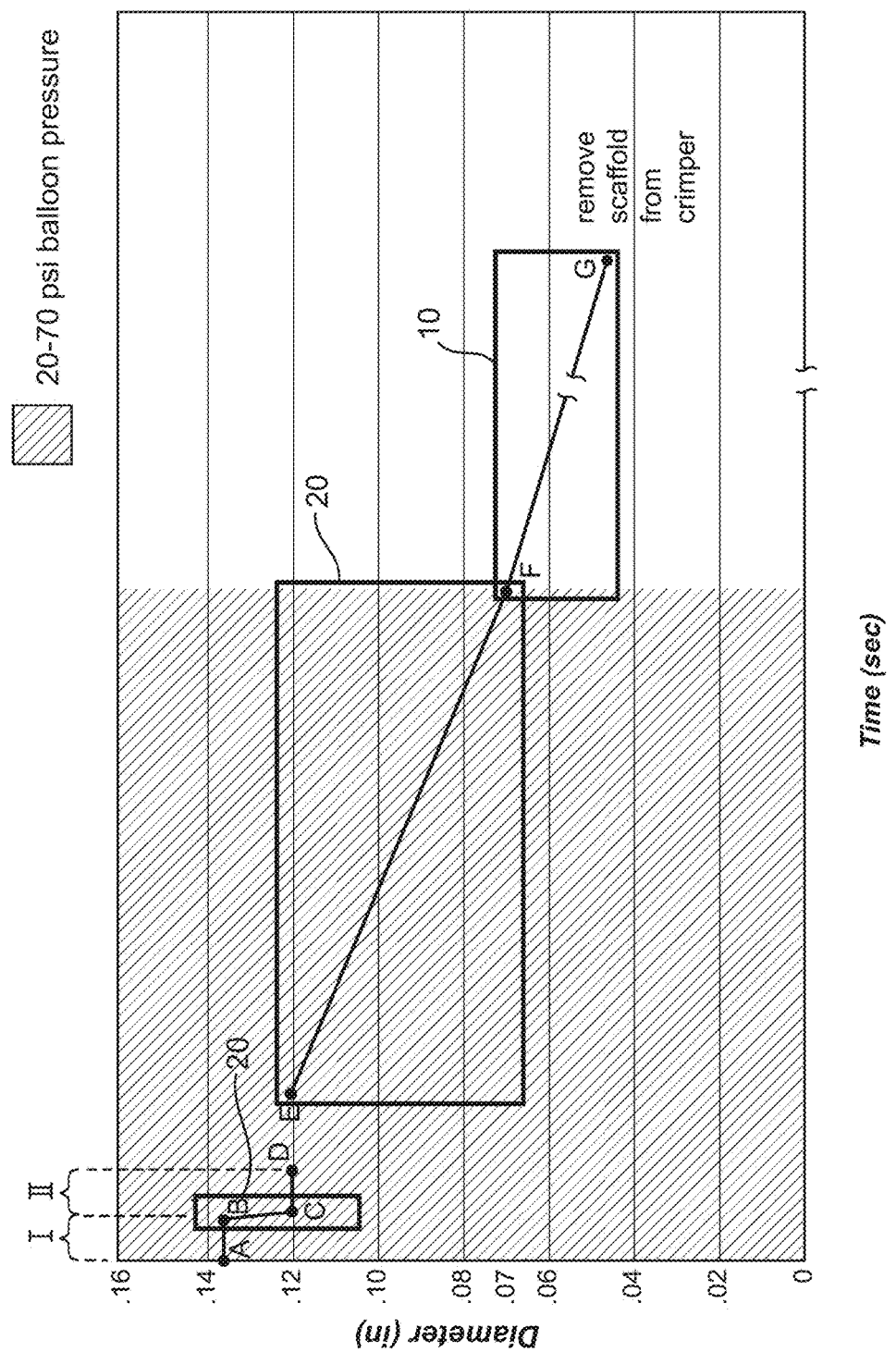
FIG. 4B shows the crimping portion of the FIG. 4A flow process in graphical form, plotting scaffold diameter vs. time and indicating the balloon pressure supplied during steps of the crimping process.

FIGS. 4A-4B illustrate the steps associated with another example of a crimping process according to the preferred embodiments. FIG. 4B illustrates in graphical form the crimping portion of the FIG. 4A flow—a graph of scaffold diameter verses time. As with the previous example, a balloon pressure of between about 20-70 psi is applied throughout substantially all of the crimping process. In this case, balloon pressure is maintained until the scaffold diameter has reached about 50% of its original diameter. Additionally, in this example, following the final alignment check the iris diameter is continuously reduced at a slow rate until reaching the final crimping diameter, and then continuous reduced further after balloon pressure is relieved. Otherwise this process is essentially the same as in Example 1.

According to the disclosure the balloon is fully or over inflated before the scaffold diameter is reduced within the crimper, or after a partial crimping and final alignment check. Additionally, balloon pressure is maintained for substantially the entire crimp process, as opposed to only during a portion of the crimping time, as was the case of the FIGS. 1A-1B examples. The balloon pressure may be maintained at more or less a constant value as in the examples or varied depending on the crimped state of the scaffold.

Continuously maintaining an inflated balloon, or gradually reducing the inflation pressure during a final dwell in combination with the other aforementioned features, such as reducing pressure when the scaffold has reached a 50% crimp, was arrived at, in part, after inspection of expanded scaffolds and balloon cross-sections for scaffolds crimped using the FIGS. 1A-1B process.

FIGS. 1A, 1B, and 1C are drawings intending to depict observed arrangements, or distributions of balloon folds when a scaffold is fully crimped using a crimping process as described the '225 application. Shown in FIGS. 1A, 1B, and 1C is a catheter shaft 4 and the balloon 8 (the crimped scaffold is not also drawn so that the balloon shapes can be more easily shown in drawings). FIG. 1A shows the arrangement of balloon folds about the circumference of the catheter shaft nearer the distal end of the balloon. FIG. 1B shows the arrangement of balloon folds about the circumference of the catheter shaft nearer the middle of the balloon. And FIG. 1C shows the arrangement of balloon folds about the circumference of the catheter shaft nearer the proximal end of the balloon (photographs of the cross-section of a scaffold crimped to a balloon, taken from the distal, middle and proximal portions of the balloon are provided in FIGS. 8A-8C).

Figure 2:
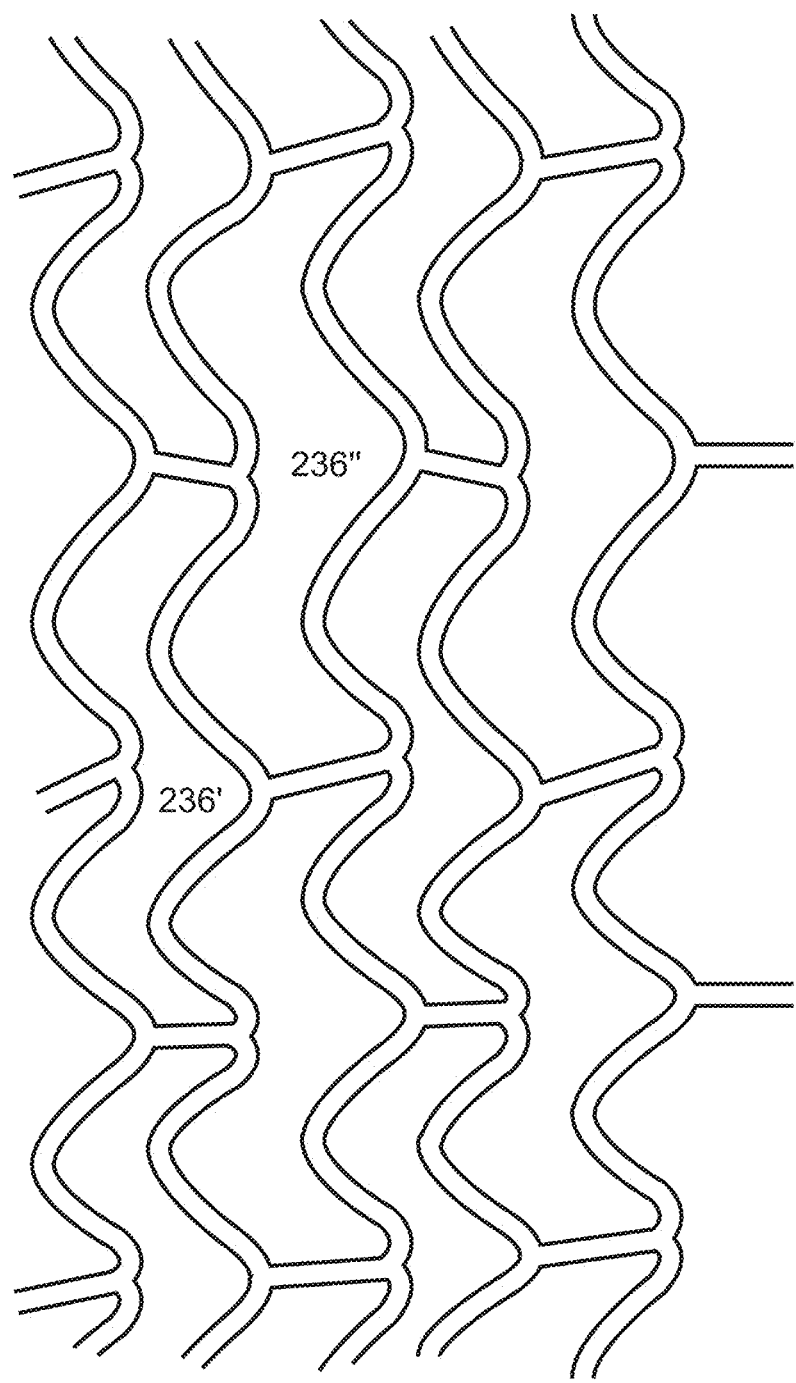
FIG. 2 shows a portion of a scaffold after balloon expansion for a scaffold crimped to a balloon using the '225 application crimping process.

As shown in each of these three drawings or photographs, about half of the circumference of the catheter shaft 4 is traversed by only a single, unfolded layer of balloon material. The remaining half of the shaft circumference has several balloon folds bunched together. When pressure is applied to a balloon having folds arranged in this manner and engaged with a crimped stent, the resulting balloon expansion will impart higher expansion forces on the scaffold struts abutting the balloon folds bunched within region A' than the struts abutting the balloon material extending over section B'. The result is a non-uniform expanded scaffold pattern, as depicted in FIG. 2 (FIG. 12A is a FINESCAN image of an expanded scaffold after crimping using the '225 application process. FIG. 9 shows an expanded scaffold. The scaffold shows a non-uniform expansion of rings and there are fractured struts.

When comparing FIG. 2 to FIG. 6 (idealized scaffold pattern after expansion), the effects of a non-uniform arrangement of balloon folds becomes apparent. The shapes of the cell regions, e.g., 236' and 236", are irregular. These irregular-shaped cells indicate that some rings have been expanded beyond their design angles while others have not been expanded to their design angles. The over-extended angles can lead to crack propagation at the crown and in some cases, failure of rings at or near the crown. While the net result is the intended expanded diameter, e.g., about 3.0 mm, the distribution of stresses among the ring struts is uneven and affects the structural integrity of the expanded scaffold.

Figure 6:
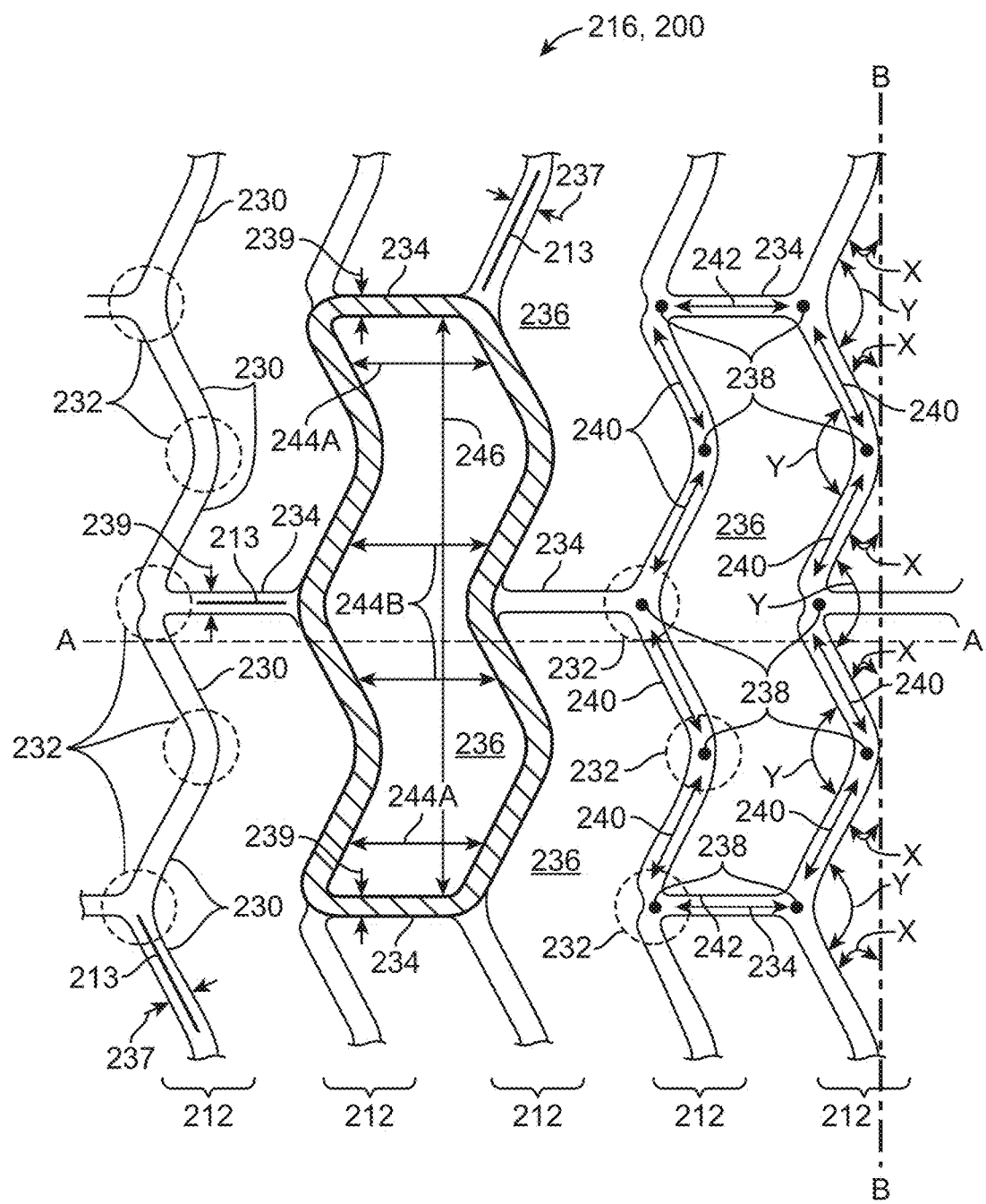
FIG. 6 shows an example of a portion of a scaffold for crimping to a balloon according to the disclosure.
Figure 7A:
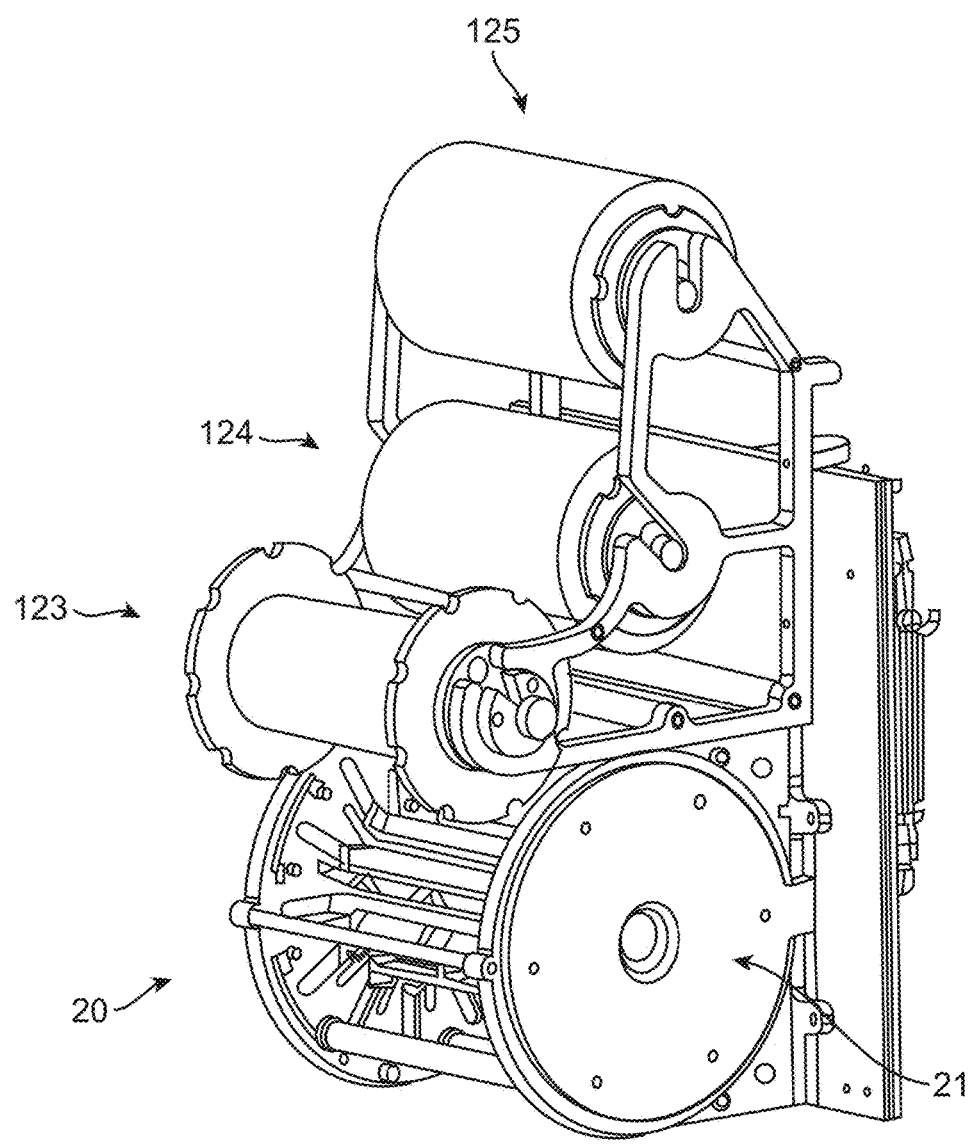
FIG. 7A is a perspective view of a prior art film-headed crimper.
Figure 7B:
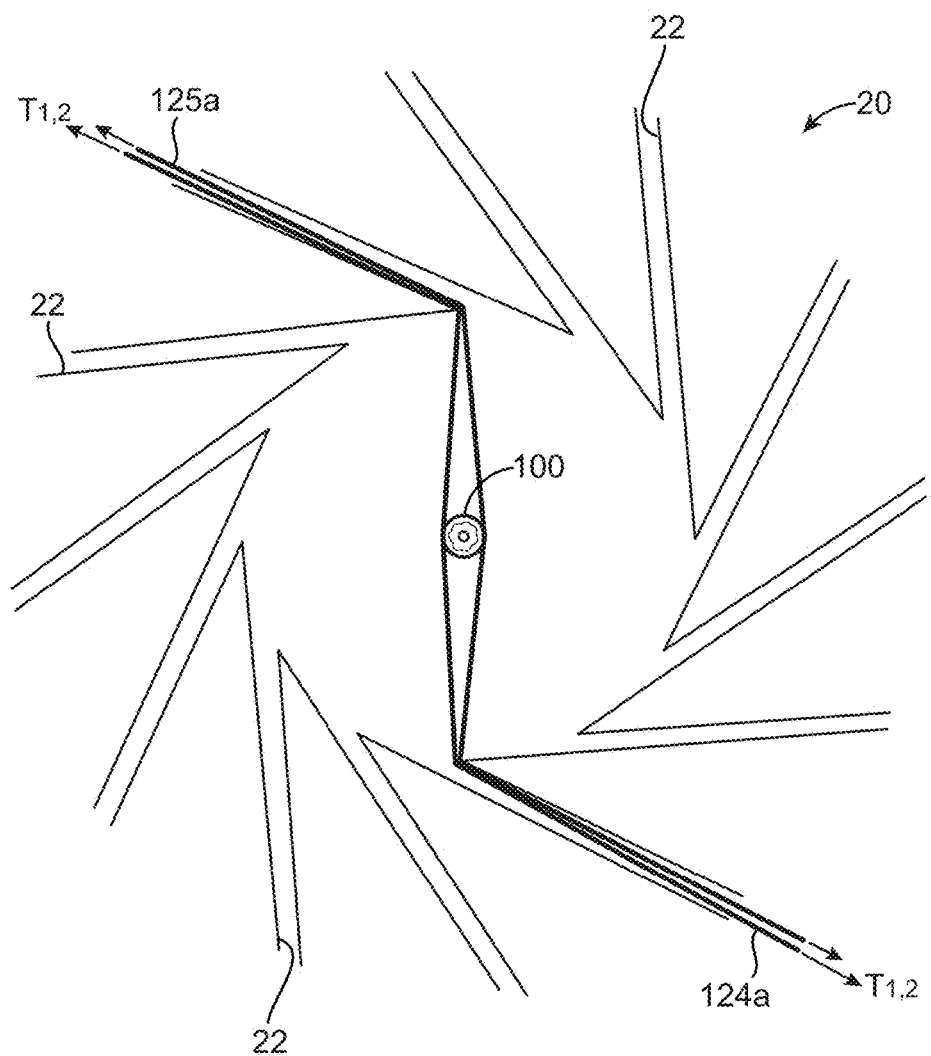
FIG. 7B is a frontal view of the head of the film-headed crimper of FIG. 7A as crimper jaws are being brought down on a stent.

As noted above, in a preferred embodiment a scaffold has the pattern described in U.S. application Ser. No. 12/447,758 (US 2010/0004735) to Yang & Jow, et al. Other examples of scaffold patterns suitable for PLLA are found in US 2008/0275537. FIG. 6 shows a detailed view of an intermediate portion 216 of a strut pattern 200 depicted in US 2010/0004735. The intermediate portion includes rings 212 with linear ring struts 230 and curved hinge elements 232. The ring struts 230 are connected to each other by hinge elements 232. The hinge elements 232 are adapted to flex, which allows the rings 212 to move from a non-deformed configuration to a deformed configuration. Line B—B lies on a reference plane perpendicular to the central axis 224 depicted in US 2010/0004735. When the rings 212 are in the non-deformed configuration, each ring strut 230 is oriented at a non-zero angle X relative to the reference plane. The non-zero angle X is between 20 degrees and 30 degrees, and more narrowly at or about 25 degrees. Also, the ring struts 230 are oriented at an interior angle Y relative to each other prior to crimping. The interior angle Y is between 120 degrees and 130 degrees, and more narrowly at or about 125 degrees. In combination with other factors such as radial expansion, having the interior angle be at least 120 degrees results in high hoop strength when the scaffold is deployed. Having the interior angle be less than 180 degrees allows the scaffold to be crimped while minimizing damage to the scaffold struts during crimping, and may also allow for expansion of the scaffold to a deployed diameter that is greater than its initial diameter prior to crimping. Link struts 234 connect the rings 212. The link struts 234 are oriented parallel or substantially parallel to a bore axis of the scaffold. The ring struts 230, hinge elements 232, and link struts 234 define a plurality of W-shape closed cells 236. The boundary or perimeter of one W-shape closed cell 236 is darkened in FIG. 2 for clarity. In FIG. 6, the W-shapes appear rotated 90 degrees counterclockwise. Each of the W-shape closed cells 236 is immediately surrounded by six other W-shape closed cells 236, meaning that the perimeter of each W-shape closed cell 236 merges with a portion of the perimeter of six other W-shape closed cells 236. Each W-shape closed cell 236 abuts or touches six other W-shape closed cells 236.

Referring to FIG. 6, the perimeter of each W-shape closed cell 236 includes eight of the ring struts 230, two of the link struts 234, and ten of the hinge elements 232. Four of the eight ring struts form a proximal side of the cell perimeter and the other four ring struts form a distal side of the cell perimeter. The opposing ring struts on the proximal and distal sides are parallel or substantially parallel to each other. Within each of the hinge elements 232 there is an intersection point 238 toward which the ring struts 230 and link struts 234 converge. There is an intersection point 238 adjacent each end of the ring struts 230 and link struts 234. Distances 240 between the intersection points adjacent the ends of rings struts 230 are the same or substantially the same for each ring strut 230 in the intermediate portion 216 of the strut pattern 200. The distances 242 are the same or substantially the same for each link strut 234 in the intermediate portion 216. The ring struts 230 have widths 237 that are uniform in dimension along the individual lengthwise axis 213 of the ring strut. The ring strut widths 237 are between 0.15 mm and 0.18 mm, and more narrowly at or about 0.165 mm. The link struts 234 have widths 239 that are also uniform in dimension along the individual lengthwise axis 213 of the link strut. The link strut widths 239 are between 0.11 mm and 0.14 mm, and more narrowly at or about 0.127 mm. The ring struts 230 and link struts 234 have the same or substantially the same thickness in the radial direction, which is between 0.10 mm and 0.18 mm, and more narrowly at or about 0.152 mm.

As shown in FIG. 6, the interior space of each W-shape closed cell 236 has an axial dimension 244 parallel to line A-A and a circumferential dimension 246 parallel to line B-B. The axial dimension 244 is constant or substantially constant with respect to circumferential position within each W-shape closed cell 236 of the intermediate portion 216. That is, axial dimensions 244A adjacent the top and bottom ends of the cells 236 are the same or substantially the same as axial dimensions 244B further away from the ends. The axial and circumferential dimensions 244, 246 are the same among the W-shape closed cells 236 in the intermediate portion 216.

It will be appreciated from FIG. 6 that the strut pattern for a scaffold that comprises linear ring struts 230 and linear link struts 234 formed from a radially expanded and axially extended polymer tube. The ring struts 230 define a plurality of rings 212 capable of moving from a non-deformed configuration to a deformed configuration. Each ring has a center point, and at least two of the center points define the scaffold central axis. The link struts 234 are oriented parallel or substantially parallel to the scaffold central axis. The link struts 234 connect the rings 212 together. The link struts 234 and the ring struts 230 defining W-shape closed cells 236. Each W-shaped cell 236 abuts other W-shaped cells. The ring struts 230 and hinge elements 232 on each ring 212 define a series of crests and troughs that alternate with each other. Each crest on each ring 212 is connected by one of the link struts 234 to another crest on an immediately adjacent ring, thereby forming an offset "brick" arrangement of the W-shaped cells.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the claims should not be construed to limit the invention to the specific embodiments disclosed in the specification. Rather, the scope of the invention is to be determined entirely by the claims, which are to be construed in accordance with established doctrines of claim interpretation.

What is claimed is:

1. A method, comprising the steps of:
providing a first balloon and a second balloon, wherein a nominal inflation diameter of the first balloon is greater than a nominal inflation diameter of the second balloon; and
crimping a stent or scaffold to the second balloon, the stent or scaffold having an outer diameter, wherein prior to the crimping the outer diameter is equal to a pre-crimp diameter, wherein the crimping to the second balloon comprises the following steps:
performing a first crimping of the stent or scaffold while the stent or scaffold is supported by the first balloon, the first crimping including reducing the outer diameter from the pre-crimp diameter to a first diameter,
replacing the first balloon with the second balloon, inflating the second balloon, and
after the first crimping, performing a second crimping wherein the stent or scaffold is crimped to the second balloon, the second crimping comprising:
while the second balloon is inflated, performing crimping steps (a), (b), (c) and (d):
(a) reducing the outer diameter to a second diameter,
(b) maintaining the second diameter for a first dwell period,
(c) reducing the outer diameter to a third diameter that is less than the second diameter, and
(d) maintaining the third diameter for a second dwell period.

2. The method of claim 1, wherein the third diameter is between 40% to 60% of the pre-crimp diameter.

3. The method of claim 1, wherein the scaffold comprises a polymer having a lower end of a glass transition temperature (TG) and during the first and second crimping the scaffold temperature is between TG and 15 degrees less than TG.

4. The method of claim 3, wherein the scaffold comprises poly (L-lactide) (PLLA) and during the first and second crimping the scaffold temperature is between 40 Deg. C. and 55 Deg. C.

5. The method of claim 2, wherein while the stent or scaffold has the third diameter,
a pressure in the inflated second balloon is decreased from a first pressure to a second pressure and the second pressure is maintained during the second dwell period.

6. The method of claim 2, wherein while the outer diameter has the third diameter the second balloon is deflated by opening a valve supplying a pressure to the balloon, and wherein the second crimping further comprises the step of reducing the outer diameter to a fourth diameter.

7. The method of claim 1, wherein the second balloon is inflated for each of the crimping steps (a), (b), (c) and (d).

8. The method of claim 7, wherein the second balloon has an inflation pressure and the inflation pressure is the same for the crimping steps (a) and (c).

9. The method of claim 1, wherein the outer diameter is greater than the first diameter after replacing the first balloon with the second balloon, and the second diameter is the same as the first diameter.

10. The method of claim 1, wherein the third diameter is about 60% of the first diameter.

11. The method of claim 1, wherein the first balloon has an overinflated state during the first crimping step.

12. The method of claim 1, wherein the second balloon has an overinflated state during the second crimping step.

13. The method of claim 12, wherein the second balloon has an overinflated state during at least steps (a) and (b).

14. The method of claim 1, wherein the second balloon is a pleated balloon and prior to the second crimping all pleats in the balloon are substantially removed.

15. A method comprising the steps of:
crimping a stent or scaffold to a balloon of a balloon catheter, the stent or scaffold having an outer diameter, wherein prior to the crimping the outer diameter is equal to a pre-crimp diameter of the stent or scaffold, the crimping comprising the following steps:
performing a first crimping to reduce the outer diameter from the pre-crimp diameter to a first diameter while supporting the stent or scaffold on an inflated first balloon having a nominal inflation diameter greater than a nominal inflation diameter of the catheter balloon;
replacing the first balloon with the catheter balloon;
inflating the catheter balloon; and performing a second crimping of the stent or scaffold to the catheter balloon, comprising:

while the catheter balloon is inflated and supporting the stent or scaffold, performing steps (a), (b), (c) and (d):

(a) reducing the outer diameter to a second diameter, (b) maintaining the second diameter for a first dwell period, (c) reducing the outer diameter to a third diameter that is less than the second diameter, and (d) maintaining the third diameter for a second dwell period.

16. The method of claim 15, wherein the first balloon has a higher burst pressure than the catheter balloon.

17. The method of claim 15, wherein an inner diameter of the stent or scaffold before the second crimping is larger than a fully inflated or over inflated diameter of the catheter balloon and equal to or less than a fully inflated or over inflated diameter of the first balloon.

18. The method of claim 15, wherein the catheter balloon is inflated for each of the steps (a), (b), (c) and (d).

19. The method of claim 15, wherein the catheter balloon is overinflated during the steps (a) and (c).

* * * * *